United States Patent [19]

Morris et al.

[11] Patent Number: 5,575,632
[45] Date of Patent: Nov. 19, 1996

[54] ENGINEERED PUMPING SEGMENT

[75] Inventors: Matthew G. Morris, San Diego; Charles E. Clemens, Encinitas; Stephen A. Martin, Carlsbad; Don S. Minami, Monte Sereno, all of Calif.; William R. George, Chicago, Ill.; Paul L. Howard, Palo Alto; Lee H. Laiterman, Los Gatos, both of Calif.

[73] Assignee: IVAC Medical Systems, Inc., San Diego, Calif.

[21] Appl. No.: 304,674

[22] Filed: Sep. 12, 1994

[51] Int. Cl.⁶ .................................................. F04B 43/08
[52] U.S. Cl. ..................... 417/477.2; 417/474; 417/63; 604/153; 128/DIG. 12
[58] Field of Search ................... 604/153; 128/DIG. 12; 73/19.1, 756, 753, 754; 417/474, 477.1, 477.2, 63

[56] References Cited

U.S. PATENT DOCUMENTS

| | | | |
|---|---|---|---|
| 4,199,307 | 4/1980 | Jassawalla | 417/474 |
| 4,236,880 | 12/1980 | Archibald | 417/478 |
| 4,273,121 | 6/1981 | Jassawalla | 128/214 F |
| 4,276,004 | 6/1981 | Hahn | 417/479 |
| 4,303,376 | 12/1981 | Siekmann | 417/360 |
| 4,493,706 | 1/1985 | Borsanyi et al. | 604/153 |
| 4,519,792 | 5/1985 | Dawe | 604/152 |
| 4,657,490 | 4/1987 | Abbott | 417/478 |
| 4,696,671 | 9/1987 | Epstein et al. | 604/67 |
| 4,842,584 | 6/1989 | Pastrone | 604/50 |
| 4,857,048 | 8/1989 | Simons et al. | 604/50 |
| 4,890,984 | 1/1990 | Alderson et al. | 417/234 |
| 5,039,279 | 8/1991 | Natwick et al. | 417/63 |
| 5,056,992 | 10/1991 | Simons et al. | 417/474 |
| 5,062,774 | 11/1991 | Kramer et al. | 417/413 |
| 5,302,093 | 4/1994 | Owens et al. | 417/474 |
| 5,322,422 | 6/1994 | Natwick et al. | 417/474 |

OTHER PUBLICATIONS

Brochure–The AVI 200 and Micro 210 Infusion Pumps with the Unique AVI Cassette.

*Primary Examiner*—Charles G. Freay
*Attorney, Agent, or Firm*—Fulwider Patton Lee & Utecht

[57] ABSTRACT

An engineered pumping segment for facilitating efficient and accurate peristaltic pumping of fluids, providing regulation of fluid flow and providing an effective interface for sensing fluid line pressure in a peristaltic pump system. The engineered pumping segment includes an elastomeric membrane sandwiched between a rigid base and a rigid cover and a slider adapted to slidably mount about the base and cover. The membrane and base define a channel for fluid flow and the membrane, base and cover cooperate to facilitate peristaltic pumping of fluids through the engineered pumping segment and to provide a pressure sensing interface, and in combination with the slider, cooperate to regulate fluid flow.

57 Claims, 11 Drawing Sheets

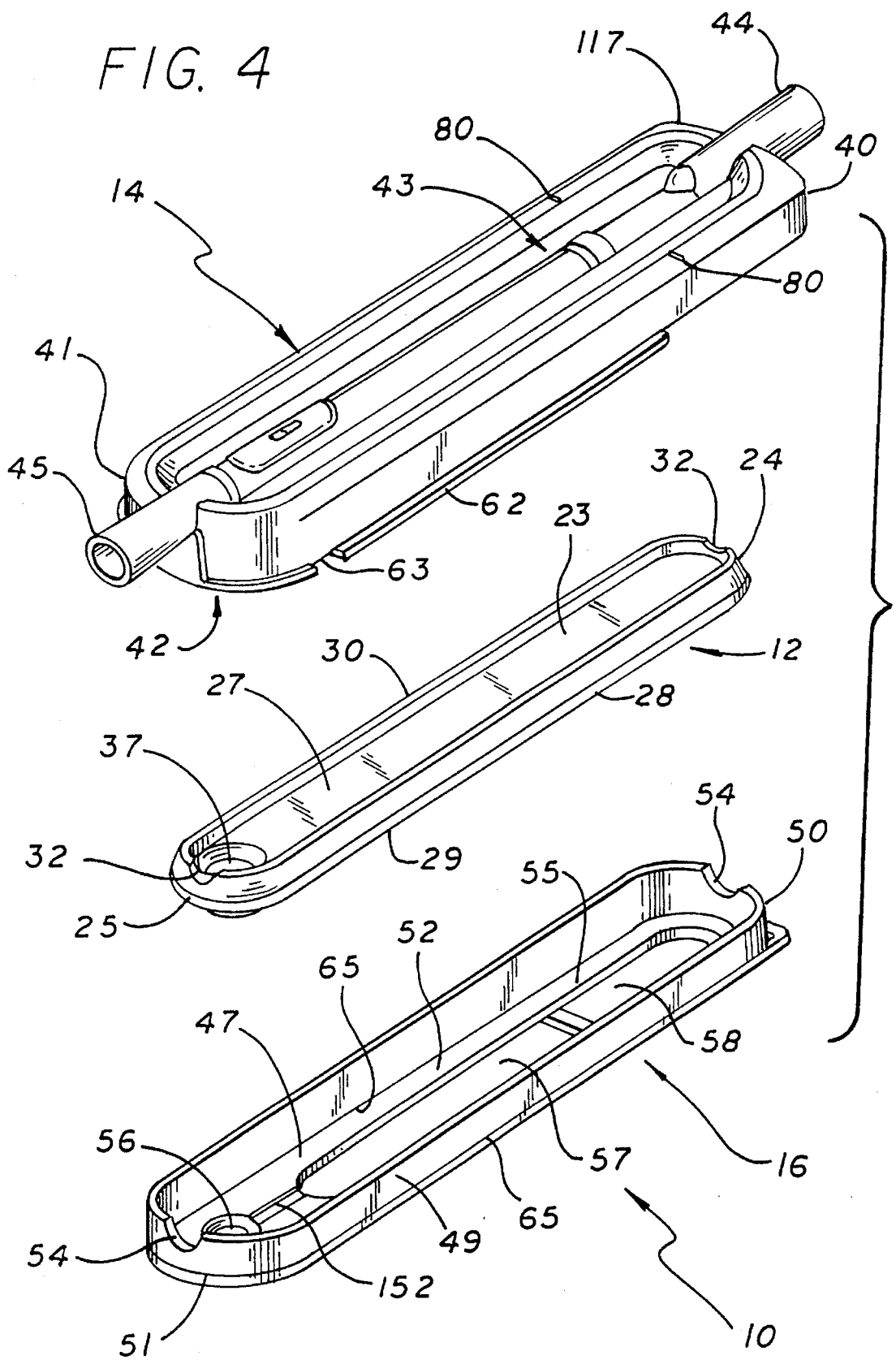

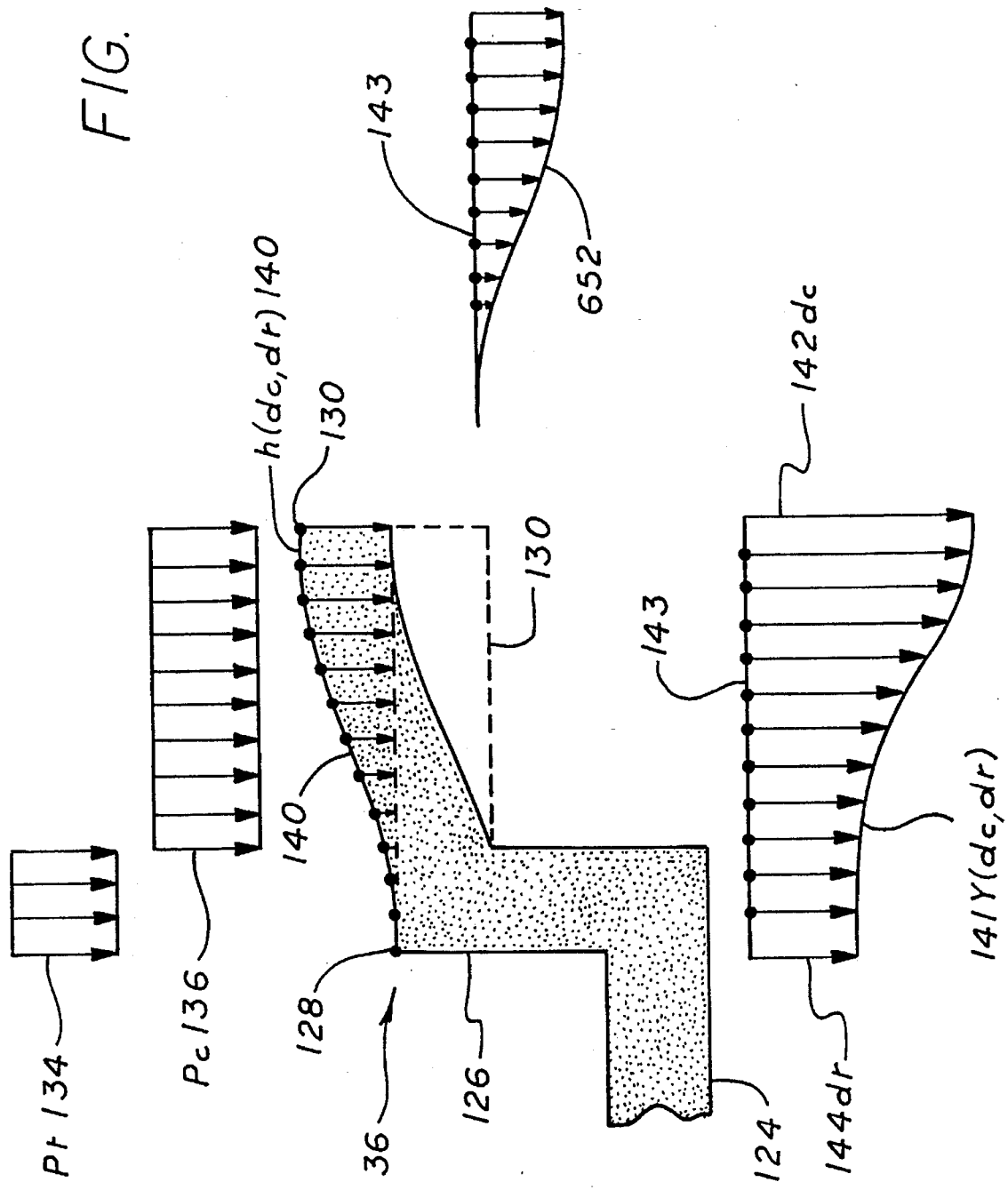

ENGINEERED PUMPING SEGMENT

BACKGROUND OF THE INVENTION

The invention relates generally to peristaltic pumping systems, and more particularly, to a pumping segment incorporated into a peristaltic pumping system that facilitates efficient and accurate peristaltic pumping of fluids as well as provides for regulation of fluid flow and an effective interface for sensing fluid pressure.

In traditional medical and industrial applications, peristaltic pumps accomplish pumping of fluids by sequentially occluding a generally round tube containing a fluid, which results in advancing fluid through the tube. It is generally the case that the tube becomes completely occluded, wherein opposing walls of the tube are brought into contact, thereby sealing the tube shut and preventing back flow. Since round tubing requires a significant degree of deformation in order to accomplish the sealing of the tube, high stress levels can be reached in the walls of the tubing.

Due to these high stress levels, the physical dimensions of the tubing may change over time, and as a result, fluid flow and fluid pressure may be affected causing deviations from expected conditions. To address this problem, some systems incorporate a tubing segment comprising materials possessing high strength and resiliency. Such tubing, however, is generally expensive relative to conventional tubing. Moreover, by merely employing a round tubing segment having greater strength and resiliency, the problems associated with the force and stress required to compress a round tube are not fully addressed.

In other applications, the pumping systems employ a separate fluid chamber contained in a pumping segment that connects to conventional tubing and that operates as structure for facilitating pumping. The typical configuration of these pumping systems is that of a piston cooperating with the chamber to pump fluid. These chambers address the problems associated with the force and stress levels in conventional round tubing but are, however, also relatively expensive to produce. In addition, systems incorporating such chambers are limited since their designs are somewhat more complex and they are more difficult and expensive to manufacture.

In a peristaltic pumping system, it is desirable to control or monitor fluid line pressure. Conventional peristaltic pumping systems typically use separate devices for accomplishing this in which one device facilitates peristaltic pumping and another device that facilitates the measurement of line pressure. Such conventional systems typically take pressure measurements directly from the tubing. However, where a peristaltic pumping system takes pressure measurements directly from the tubing, tubing dimensions and elastic properties must be accurately and closely controlled to assure precise measurements.

Also, in order to take accurate pressure measurements, it is important that the peristaltic pumping system employs structure that assures an effective interface between the fluid pressure and the pressure sensing element. Conventional systems that take fluid pressure measurements directly from the tubing are limited, since they often lack an optimum interface between the tubing and sensor. Generally speaking, a significant negative pressure that may accumulate in the tubing can cause the interfacing structure of conventional systems to separate from the sensor, thereby preventing transfer of fluid pressure to the sensor.

In peristaltic pumping systems, it also may be desirable to provide an automatically operated flow control device that operates on the fluid conduit but which also permits manual operations. Conventional systems generally incorporate fluid flow regulation capabilities into a separate device from those functioning to facilitate the peristaltic pumping of fluids and those functioning to facilitate measurement of fluid line pressure. Such conventional fluid flow regulators heretofore provided have utilized various clamp, lever or roller arrangements for partially or completely crimping flexible round tubing at a point upstream from the pumping mechanism. One conventional flow control device includes a ribbed roller having ends which travel within laterally spaced apart furrows formed in vertical sidewalls of a housing through which flexible round tubing of the pumping system passes. The housing also includes an opposing wall that is inclined at an angle to the path of the roller and the housing receives the round tubing between the path of the roller and the opposing wall. By varying the position of the roller along the furrows, the degree of tubing closure and hence the flow rate of fluid through the system, can be controlled.

Flow control devices of this type, however, are limited in that the flexible tubing they act upon can be flattened or otherwise dimensionally deformed as a result of the compression force exerted by a clamp, lever or roller over a period of time. This deformation or creep may progress with time, with the result that the flow rate in the system changes from an expected rate, and the system therefore, requires the user to periodically readjust the flow control device in order to achieve desired flow rates.

Other fluid control devices embody a flexible round conduit that connects with and replaces a segment of conventional tubing and includes a cylindrical insert member disposed within the conduit. The cylindrical insert defines a channel for fluid flow, a portion of which has a progressively increasing cross-sectional area along its axis. An outer sleeve fits over the flexible cylindrical conduit and embodies a roller that slides within a track formed in the outer sleeve. By positioning the roller along the flexible cylindrical conduit, portions of the flexible conduit are forced into the channel defined by the cylindrical insert, thereby controlling fluid flow. This device, however, is limited since the cross-sectional area of the cylindrical conduit may change with time and therefore, require the user to make adjustments to achieve desired flow rates. Moreover, the device is limited since it embodies a relatively complex design having a number of interacting and moving parts that require high precision manufacturing with associated increased expense.

Accordingly, there remains a need for a single device that facilitates efficient and accurate peristaltic pumping of fluids over long periods of time, that provides an effective interface for sensing fluid pressure under varying conditions of line pressure, including negative pressure, and that provides regulation of fluid flow while minimizing system inaccuracies. The present invention fulfills these needs.

SUMMARY OF THE INVENTION

Briefly and in general terms, the present invention provides an engineered pumping segment that incorporates, into a single device, structure which facilitates efficient and accurate peristaltic pumping of fluids, regulates fluid flow and provides an effective interface for sensing internal pressure. The engineered pumping segment in accordance with the invention includes a portion functioning as a pumping segment in a peristaltic pump, a portion functioning as a fluid flow regulator and a portion functioning as a pressure diaphragm that allows measurement of internal fluid pressure by standard pressure transducer means.

In the preferred embodiment, the engineered pumping segment has a resilient elastomeric membrane sandwiched between a rigid base and a rigid cover and a slider adapted to receive a ball and adapted to slidably mount upon the rigid base and cover. At each end of the engineered pumping segment are tubing fittings adapted to receive typical tubing of a peristaltic pump system. Formed into and extending substantially the length of the base is a groove which in conjunction with the elastomeric membrane, defines a channel through which fluid flows.

Proximate to one end of the engineered pumping segment, the elastomeric membrane and the cover form a pressure measurement area. In the preferred embodiment, the elastomeric membrane is formed into a flexible dome-shaped vessel that extends away from and substantially perpendicular to the engineered pumping segment and is adapted to be in continuous and direct contact with a pressure sensitive region of a sensor, even in situations where there is a negative pressure in the fluid line.

An intermediate portion of the preferred embodiment of the engineered pumping segment forms a fluid flow conduit having a specific cross-sectional shape that is defined by the rigid base and elastomeric membrane. This intermediate portion functions as the pumping section of the engineered pumping segment.

At another end, the engineered pumping segment includes a fluid flow regulator. The fluid flow regulator permits control over the rate of flow including the ability to completely stop flow. In a more detailed aspect, the regulator includes a slider adapted to receive a ball and adapted to slidably mount about and interact with the cover, membrane and base. The slider travels longitudinally along an end portion of the engineered pumping segment designated the fluid control region, which includes a variable depth and/or width groove having a cross-sectional area varying from zero to a value suitable for allowing a maximal desired flow rate.

Other aspects and advantages of the invention will become apparent from the following detailed description, taken in conjunction with the accompanying drawings, which illustrate, by way of example, the principles of the invention.

BRIEF DESCRIPTION OF THE DRAWINGS

FIG. 4 is an exploded view of the engineered pumping segment of FIG. 1 from the upper side view perspective and without the slider;

FIG. 16 is schematic cross-sectional representation of the pressure vessel portion of the engineered pumping segment of FIGS. 14 and 15, showing pressures applied thereto.

DETAILED DESCRIPTION OF THE PREFERRED EMBODIMENTS

Figure 1:
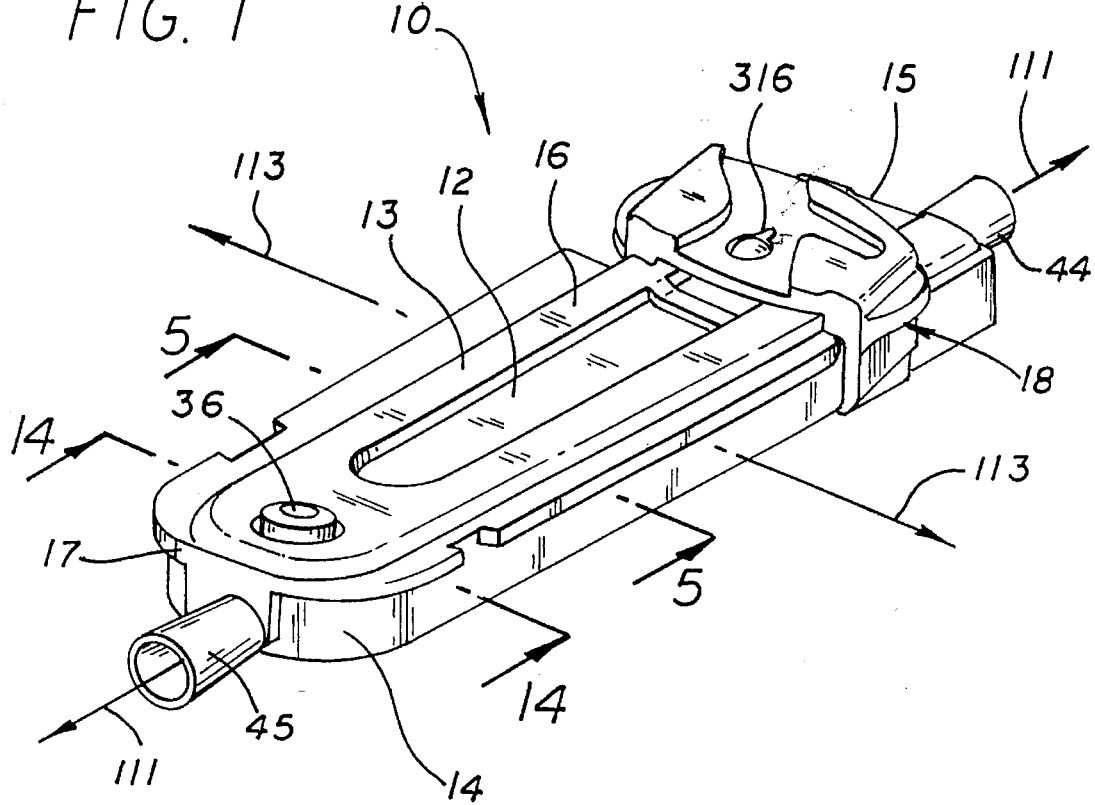
FIG. 1 is a perspective view of the preferred embodiment of the present invention, illustrating an upper side of an engineered pumping segment.

As is shown in the drawings, which are provided for purposes of illustration and not by way of limitation, the invention is embodied in an engineered pumping segment that, in a single device, facilitates effective and accurate pumping of fluids in a pumping system, regulates fluid flow, and provides an effective interface for sensing fluid pressure.

Referring now to the drawings, and more particularly to FIG. 1, there is shown an engineered pumping segment 10. Generally, the engineered pumping segment 10 is a device that is to be releasably mounted to a pumping system (shown in FIG. 10) which functions to control the transfer of fluid from a reservoir to a delivery site. The pumping system delivers fluid from the reservoir to a proximal end 15 of the pumping segment 10 by way of conventional tubing. The fluid passes through the pumping segment 10 and exits a distal end 17 of the pumping segment 10. Attached to the distal end 17 is additional conventional tubing of the pumping system that transports the fluid away from the pumping segment 10 and towards the delivery site.

Figure 5:
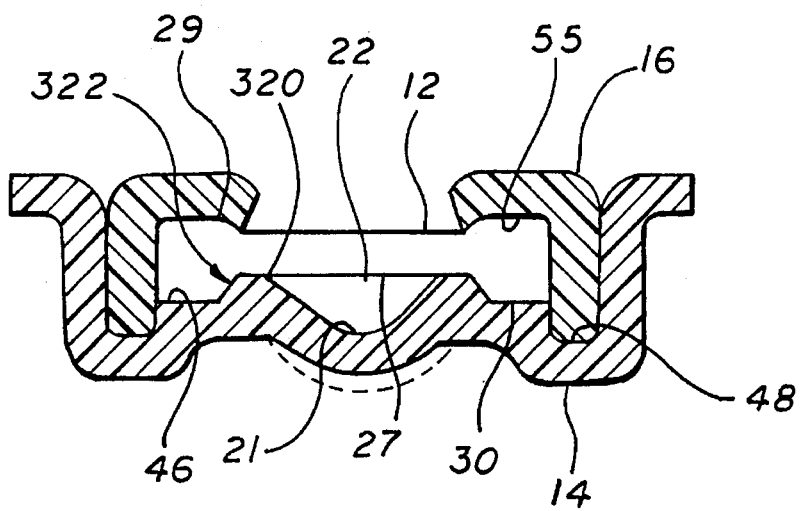
FIG. 5 is an enlarged cross-sectional view taken along lines 5—5 of FIG. 1.

The engineered pumping segment 10 includes three basic components. As is best seen in FIG. 5, which is a cross-sectional view, the preferred embodiment of the engineered pumping segment 10 includes an elastomeric membrane 12 that is sandwiched between a base 14 and a cover 16. When assembled, the cover 16 is either level with or below the height of the base 14. As shown in FIG. 5, the cover is level with the base flange. Generally, the path that fluid takes through the pumping segment 10 is defined by the membrane 12 and the base 14. The cover 16 generally functions to sealingly retain the membrane 14 against the base 14 as well as against itself. The configurations of the membrane 12, base 14 and cover 16 will be described in detail below.

The pumping segment 10 performs three different functions. Near the proximal end 15 of the engineered pumping segment 10, there is structure functioning to regulate flow rates through the pumping segment 10. In an intermediate section 13 of the pumping segment 10, there is structure adapted to cooperate with the pumping system to peristaltically pump fluids through the pumping segment 10. Near its distal end 17, the pumping segment 10 has structure adapted to cooperate with the pumping system to sense the pressure of fluid passing through the pumping segment 10.

Fluid flow regulation is generally accomplished in the pumping segment 10 through the cooperation of the use of a slider 18. The configuration of the slider 18 will be described in detail below. Near the proximal end 15 of the pumping segment 10, the cover 16 provides access to the elastomeric membrane 12. By way of the access provided by the cover 16, the slider 18 functions to depress the membrane 12 against the fluid flow path, whereby the cross-sectional area through which fluid may flow is altered. As the slider 18 travels along the base 14 it depresses the membrane 12 sealingly against the base 14 thus occluding flow except in the variable cross-section groove 60. By altering the fluid flow path and by doing so to varying degrees, the slider 18 regulates the flow of fluid through the pumping segment 10.

Turning now to the peristaltic pumping of fluids through the pumping segment 10, peristaltic pumping is facilitated primarily through the cooperation of the membrane 12 and base 14 of the pumping segment 10. At the intermediate section 13 of the pumping segment 10, the cover 16 provides further access to the membrane 12, through which a peristaltic pumping mechanism (not shown) of the pumping system operates. Generally, the peristaltic pumping mechanism operates to sequentially alternatively depress adjacent portions of the membrane 12 against the fluid flow path against the groove in the base 14 to thereby advance fluid through the pumping segment 10.

Pressure sensing of fluids flowing through the pumping segment 10 is facilitated primarily through the cooperation of the membrane 12 and cover 16 of the pumping segment 10. Near the distal end 17 of the pumping segment 10, the cover 16 again provides access to the membrane 12. In this area, the membrane 12 is formed into a generally hollow and flexible closed cylinder having a crown, part of which includes a dome-shaped section. For convenience in description, the vessel 36 is referred to as a dome-shaped pressure vessel 36. The vessel acts as a pressure diaphragm for transferring pressure information regarding the fluid flowing through the pumping segment 10.

Now that the basic functions and components of the engineered pumping segment 10 have been identified, a more detailed description of the structure of the pumping segment 10 will follow. The overall configuration of the pumping segment 10 is first described followed by basic descriptions of the overall configurations of the components of the pumping segment 10. Thereafter, the details of the components and their functions are individually addressed as well as their cooperation with associated structure of the pumping system to which the pumping segment 10 is releasably mounted.

In the preferred embodiment, as shown in FIG. 1, the engineered pumping segment 10 is elongate in shape with longitudinal and lateral axes 111, 113. The length of the elongate pumping segment 10 is greater than both its width and its height and the width of the pumping segment 10 is greater than its height.

The overall length of the pumping segment 10 shown was selected in accordance with anthropometric studies to be approximately equal to the average (fifty percentile) adult female hand width so that the segment 10 can be pressed with some fingers to the palm and the thumb can manipulate the slider 18. Thus, one-handed operation of the pumping segment 10 is greatly facilitated.

The overall outer configuration of the pumping segment 10, when viewed so that its entire width can be seen, generally approximates an elongated oval with one of its ends being truncated. The proximal end 15 of the pumping segment 10 includes the truncated portion of the elongated oval and the distal end 17 includes the rounded end of the elongated oval.

Extending from the proximal end 15 and parallel to the longitudinal axis 111 of the elongate pumping segment 10 is a cylindrical tubing fitting 44 that is adapted to attach to conventional tubing of the pumping system and that defines an entrance for the passage of fluid into the pumping segment 10. Similarly, extending from the distal end 17 and parallel to the longitudinal axis 111 of the pumping segment 10 is another cylindrical tubing fitting 45 that also is adapted to attach to conventional tubing of a pumping system and that defines an exit port for fluid passing through the pumping segment 10.

Figure 2:
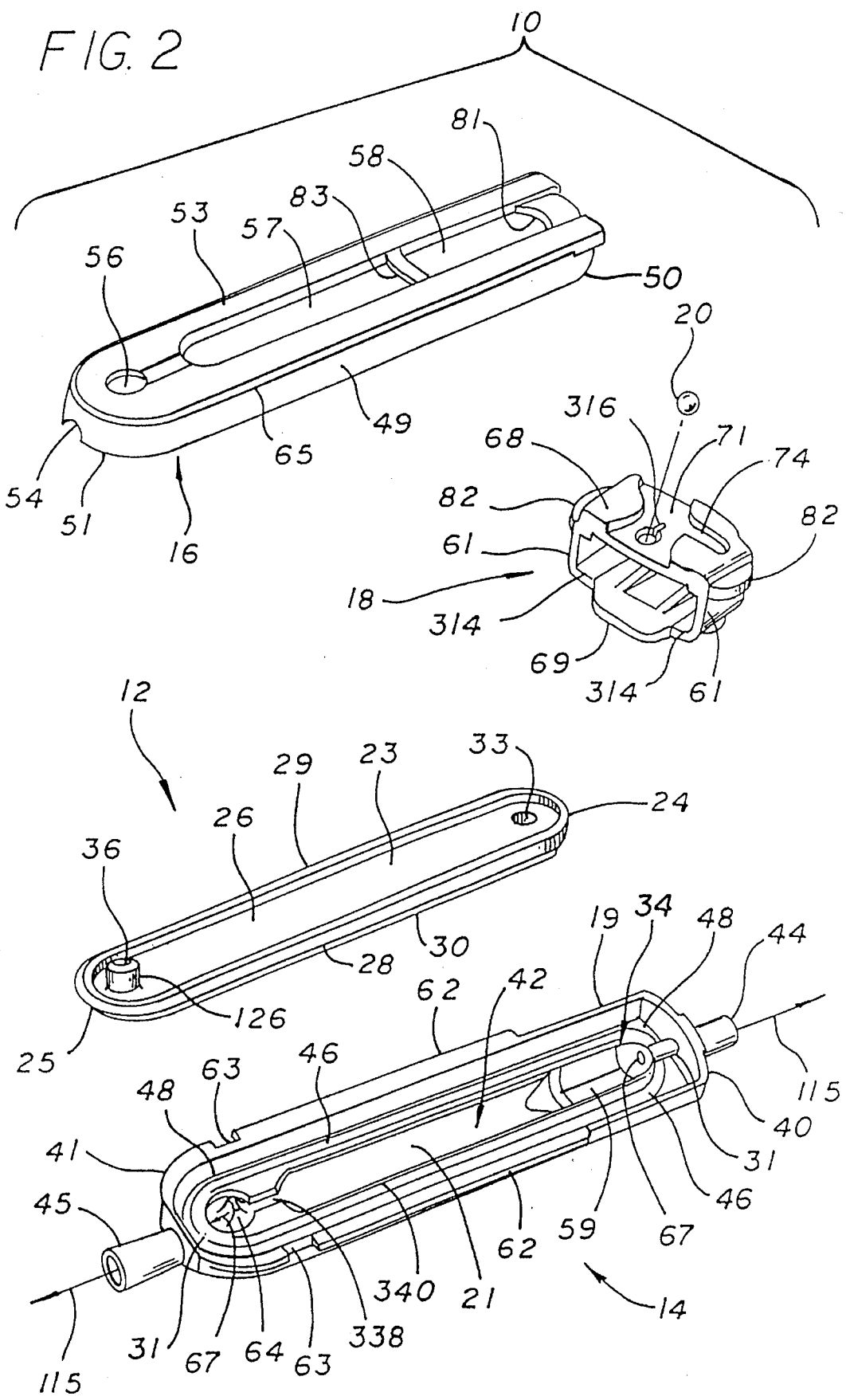
FIG. 2 is an exploded view of the engineered pumping segment of FIG. 1 showing the base, the membrane, the cover, and the slider from the lower side view perspective.

The overall configurations of the base 14, cover 16, membrane 12 and slider 18 are described next. Referring now to FIG. 2, which is an exploded view of the pumping segment 10, the base 14 generally defines the overall truncated oval-shaped configuration of the pumping segment 10 as described above and includes the cylindrical tubing fittings 44, 45. The base 14 is formed of a bottom portion 34 and a sidewall 19 which extends substantially around a perimeter 63 of the bottom portion 34. The sidewall 19 and bottom portion 34 define an interior region 42 of the base 14. A groove 21 formed in the bottom portion 34 of the base 14 and parallel to the longitudinal axis 111 of the pumping segment 10 defines a lower portion of a channel 22 (see FIG. 5) for fluid flow. As will be addressed in more detail later, the channel 22 communicates with the tubing fittings 44, 45.

Referring now to FIG. 4, which is an upside down exploded view of the pumping segment 10 without the slider 18, the overall configuration of the cover 16 is described. The cover 16 has a generally matching (relative to the base 14) truncated oval-shaped configuration, with a generally planar top portion 47 and a sidewall 49 extending therefrom in a substantially perpendicular manner substantially around a perimeter 65 thereof to define an interior region 52 within the cover 16. At a proximal end 50 of the cover 16, rather than following the truncated oval-shaped perimeter 65 of the cover 16, the sidewall 49 forms a semi-circular shape that mimics a semi-circular shape of the sidewall 49 extending from a distal end 51 of the cover 16. As such, the sidewall 49 has an elongate oval-shaped configuration that is not truncated.

The overall configuration of the cover 16 is slightly smaller than that of the base 14 and is adapted so that the perimeter 65 and sidewall 49 of the cover 16 snugly fit within the sidewall 19 of the base 14 when the cover 16 is placed within the base 14 with the interior region 52 of the cover 16 facing the interior region 42 of the base 14. Further, the sidewall 49 of the cover 16 is adapted to fit around a perimeter 28 of the membrane 12.

The overall configuration of the membrane 12 is depicted in FIG. 2. The perimeter 28 of the membrane 12 has a generally elongated and oval-shaped overall configuration that is adapted to sealingly seat within the interior region 42 of the base 14 and the interior region 52 of the cover. The oval-shaped membrane 12 includes a proximal rounded terminal end 24, a distal rounded terminal end 25 and a central planar region 23. A concavity 33 is included adjacent the proximal end 24. In the embodiment shown, it is oval in overall shape and the membrane is thinner, although the underside of the membrane remains planar. The ball 20 of the slider, as discussed below in detail, fits into the concavity 33 at the full flow position. The reduced amount of membrane material at this position reduces the chances of the ball depressing the membrane into the groove and then reducing the amount of flow. The other details of its configuration, including those relative to the hollow and flexible dome-shaped pressure vessel 36, will be described in more detail below.

As can be noted, the membrane is flexible and a change in head height can cause it to move away from or closer to the conduit 22 which results in a change in the fill volume of the conduit. The distance across the membrane, width and depth of the groove were selected so that only a four percent change of the fill volume of the pumping segment would occur if the fluid reservoir were moved to result in a pressure change of 30 inches of water. In one embodiment, this resulted in a change of 2.4 µl.

Also, in the preferred embodiment, the engineered pumping segment 10 includes the slider 18. The slider 18 is adapted to fit around and travel along a portion of the pumping segment 10 near its proximal end 15. The motion of the slider 18 along the pumping segment 10 is parallel to the longitudinal axis 111.

As shown in FIG. 2, the overall configuration of an embodiment of the slider 18 generally approximates a hollow rectangular sleeve, and since it fits around the pumping segment 10, the slider 18 also has a width that is greater than its height. Further, the length of the slider 18 is less than its width and is similar in magnitude to its height. The slider 18 is adapted to receive a ball 20.

Additional details of the individual components of the pumping segment 10 will now be discussed. The membrane 12 may be produced by liquid injection molding or by other methods and may comprise an elastomeric material, such as silicone GE 6030 made by; General Electric, having sufficient strength and resiliency so that it may repeatedly perform desired functions efficiently and with accuracy over a relatively long period of time. Referring to FIG. 2, the upper surface 26 of the membrane 12 is best seen. The upper surface 26 includes a central planar region 23. Extending the entire perimeter 28 of the upper surface 26 and projecting from the central planar region 23 of the membrane 12, is an upper sidewall 29. The upper sidewall 29 is configured so that it forms a first sealing relationship with the cover 16. Located near the distal terminal end 25 of the membrane 12 and projecting from its central planar region 23, is the flexible dome-shaped pressure vessel 36 which functions as the pressure diaphragm. The dome-shaped pressure vessel 36 has a cylindrical sidewall 126 and extends a predetermined distance from the upper surface 26 of the membrane 12 so as to create an interface that may be preloaded against and in direct contact with a pressure sensor (shown in FIG. 12 and discussed further below).

Referring now to FIG. 4, a lower surface 27 of the membrane 12 is shown. The lower surface 27 also includes a central planar region 23. Extending the entire perimeter 28 of the membrane 12 and projecting from the central planar region 23 of the lower surface 27 is a lower sidewall 30. The lower sidewall 30 is configured so that it forms a second sealing relationship with the base 14. Formed at the terminal ends 24, 25 of the membrane 12 and in the lower sidewall 30 are semi-circular archways 32 which engage associated structure of the base 14 defining the entrance and exit to the channel 22 for fluid flow. The lower surface 27 of the membrane 12 also includes a cavity 37 that forms the underside of the hollow and flexible dome-shaped vessel 36.

Turning again to FIG. 2; additional details of the base 14 are described. The interior 42 of the base 14 includes structure that is configured to receive and mate with the sidewall 49 of the cover 16 and the lower sidewall 30 of the membrane 12. Accordingly, formed in the interior 42 of the base 14 is an oval membrane recess 46 adapted to receive and seal with the oval lower sidewall 30 of the membrane 12. Further, an oval cover recess 48 adapted to receive the oval sidewall 49 of the cover 16 is formed in the interior 42 of the base 14. The membrane and cover recesses 46, 48, therefore, form concentric oval-like troughs in the base 14, with the membrane recess 46 residing inwardly of the cover recess 48.

Formed near each end 40, 41 of the base 14 and in either end of the oval cover recess 48, are elongate rounded projections 31 lying in parallel with a longitudinal axis 115 of the base 14. The rounded projections 31 each have an internal bore 67 (only the bore in the proximal rounded projection 31 can be seen in the drawings) and each are in fluid communication with an associated tubing fitting 44, 45 to thereby provide inlets and outlets to the interior 42 of the base 14. Further, near the distal end 41 of the base 14 and in the groove 21, the interior 42 of the base 14 has formed therein an upwardly extending protrusion which acts as a bubble ejector 64.

Figure 12:
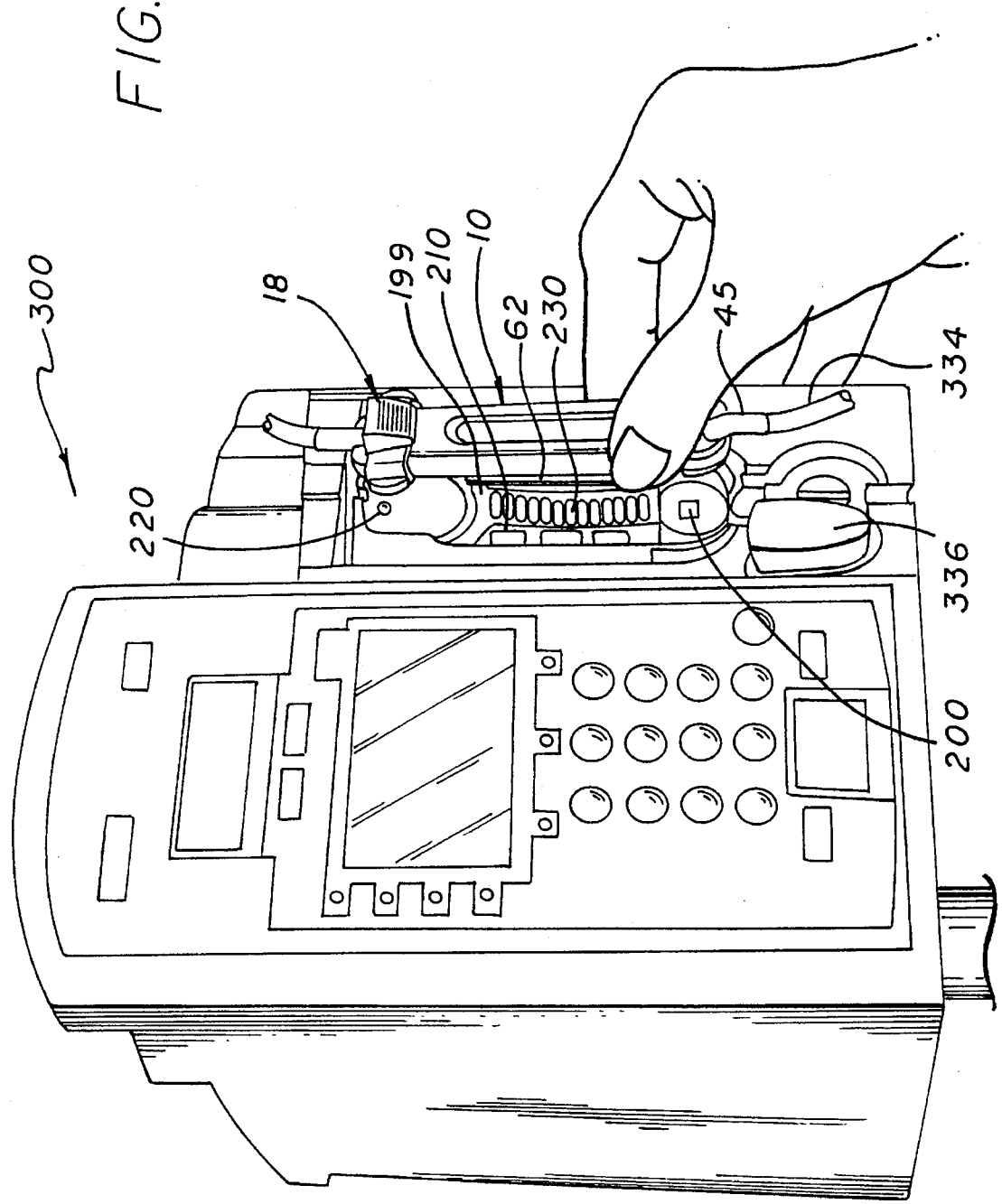
FIG. 12 is a perspective view of the engineered pumping segment of FIG. 1, shown being placed into an infusion system.

The outlet fitting 45 has a length selected to result in less curvature of the attached fluid line near the pumping segment 10. As shown in FIG. 12, the pumping segment 10 is being installed in a pump 300. The outlet fitting 45 has a flexible fluid line tubing 334 that is directed towards an air-in-line sensor system 336 and is meant to be captured by the air-in-line system as it rotates into position. Because the outlet fitting 45 is relatively rigid, the fluid tubing 334 does not begin any curl it may acquire from packaging until some point downstream from its point of connection with the outlet fitting 45. The length of the outlet fitting is selected to move this curl point as far downstream as possible so that the tubing is less likely to curl severely before the air-in-line sensor.

Figure 6:
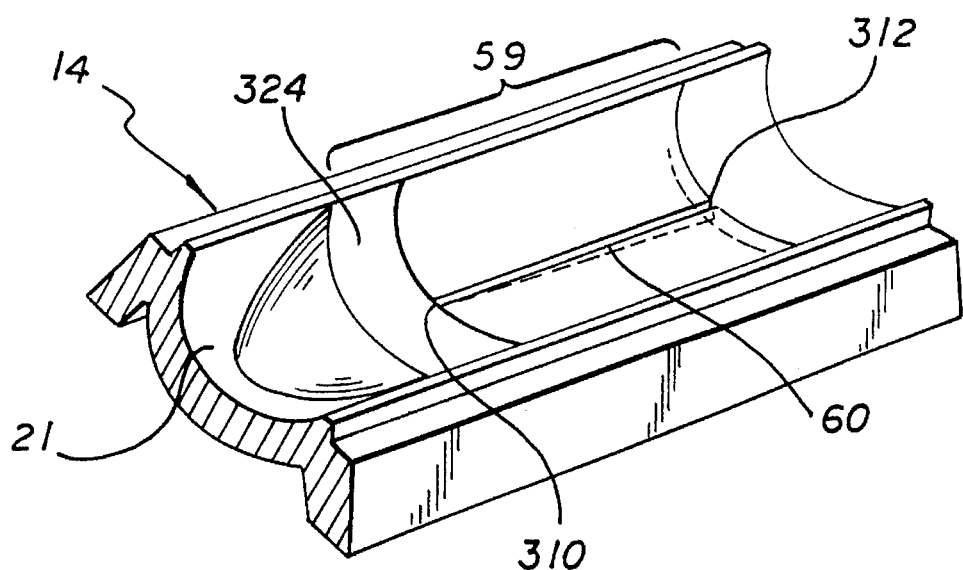
FIG. 6 is an enlarged fragmentary view of the fluid regulation portion of the base of the exploded engineered pumping segment shown in FIG. 2.

Referring to FIGS. 2 and 6, near a proximal end 40 of the base 14, the groove 21 has an elevated section that operates as a fluid control region 59. Formed in the fluid control region 59 and extending parallel to a longitudinal axis 115 of the base 14 is another groove 60 having a variable depth and/or width (variable cross-section size) and a cross-sectional area ranging from zero 310 to some desired depth 312 suitable for allowing a maximum desired flow rate.

The base 14 also includes a flange 62 extending substantially perpendicularly from the top of the sidewall 19 of the base 14 and away from the interior 42 of the base 14. The flange 62 is formed about the distal end 41 and on either side of the midsection of the base 14 and terminates at parallel longitudinal locations on either side of the base 14 distal to the longitudinal position of the fluid control region 59. Further, rectangular notches 63 are cut into the flange 62 at parallel longitudinal locations along the base 14 near the distal end 41 of the base 14.

As shown in FIG. 4, formed on an exterior 117 of the base 14 are two click stops 80, which are two upwardly extending low profile projections. The click stops are spaced laterally apart at the same longitudinal position along the base 14 and are located near where the flange 62 terminates. Corresponding click stop upwardly extending projections 314 are also located on the slider (FIG. 2). The interaction of these click stops 80 and 314 provides an affirmative sensory indication to an operator of the slider 18 attaining a predetermined position, in this case, the flow stop position. An audible sound is also generated.

Continuing to refer to FIG. 4, the details of the cover 16 are next described. The cover 16 is elongate and has proximal and distal terminal ends 50,51 and a generally concave interior 52 and a generally convex exterior 53. Formed in the sidewall 49 at each terminal end 50,51 of the cover 16 are cover recesses 54 which approximate semi-circles and which are adapted to receive the elongate rounded projections 31 of the base 14. Within the interior 52 of the cover 16 is an oval-shaped membrane indentation 55 configured to receive and mate with the generally oval shaped upper sidewall 29 of the membrane 12.

In the preferred embodiment, the cover 16 also has apertures which, when the pumping segment 10 is in its assembled form, provide access to various portions of the membrane 12. A circular aperture 56 is formed near the distal terminal end 51 and substantially in the center of the width of the cover 16. Surrounding the aperture 56 is a projection 152 that assists in centering the membrane during assembly of the pumping segment 10. The projection 152 proceeds completely around the aperture 56 and interacts with the pressure vessel 36 portion of the membrane to center it in the aperture 56 during assembly of the segment 10. Without the projection, the vessel may tend to move longitudinally during manufacture and be located off center when assembled.

Formed in an intermediate portion of the cover and also substantially centered in its width, is an elongate intermediate aperture 57. Finally, an elongate fluid control aperture 58 is centered in the cover 16 near the proximal terminal end 50 of the cover 16.

Referring now to FIG. 2, a channel 338 is formed between the pumping section 340 of the base and the pressure vessel 36 section. This channel 338 has dimensions selected to lessen the transmission of pumping noise from the pumping section 340 to the pressure sensing section 36. In the embodiment shown, the length of the channel 338 was selected to be three times its width. It was found that these dimensions decreased the amount of pumping noise reaching a sensor coupled to the pressure vessel 36.

The base and cover were, in one embodiment, made from polymer acrylic such as acrylic cyro XT250 from Cyro Industries, 100 Valley Road, Mt. Arlington, N.J.

Next, in referring to FIG. 2, additional details of the slider 18 are described. As mentioned above, in the preferred embodiment, the slider 18 is adapted to receive a ball 20. In one embodiment, the ball was formed of stainless steel and the slider was formed of acetal polymer such as BASF W2320 from BASF, 100 Cherry Hill Road, Parsippany, N.J. The slider 18 is a generally hollow structure having a generally rectangular cross-section and a sufficient length to facilitate manipulation by hand. The slider 18 has a first long side 68 and a second long side 69 and a pair of short sides 61 completing the generally rectangular cross-sectional shape. The exterior of the slider is smooth without sharp edges so that it is less likely to catch on anything in its environment of use (such as operator clothing) and be moved inadvertently.

Formed in substantially the center of the first long side 68 is a groove 74. The configuration of the groove 74 resembles a palm view of a right hand without fingers, but including a thumb pointing towards one of the short sides 61 and including a portion of what may be described as a wrist extending therefrom. Formed substantially in the center of the first long side 68 and within the groove 74, is a socket 71 which is adapted to receive and retain the ball 20. The diameter of the socket 71 is less than the diameter of the ball 20; hence, once the ball has been pressed through the socket 71, the socket retains the ball between it and the membrane. Further, formed into the short sides 61 of the slider 18 and extending the length of the slider 18 and substantially perpendicularly therefrom, are rounded low-profile projections or ears 82.

Figure 3:
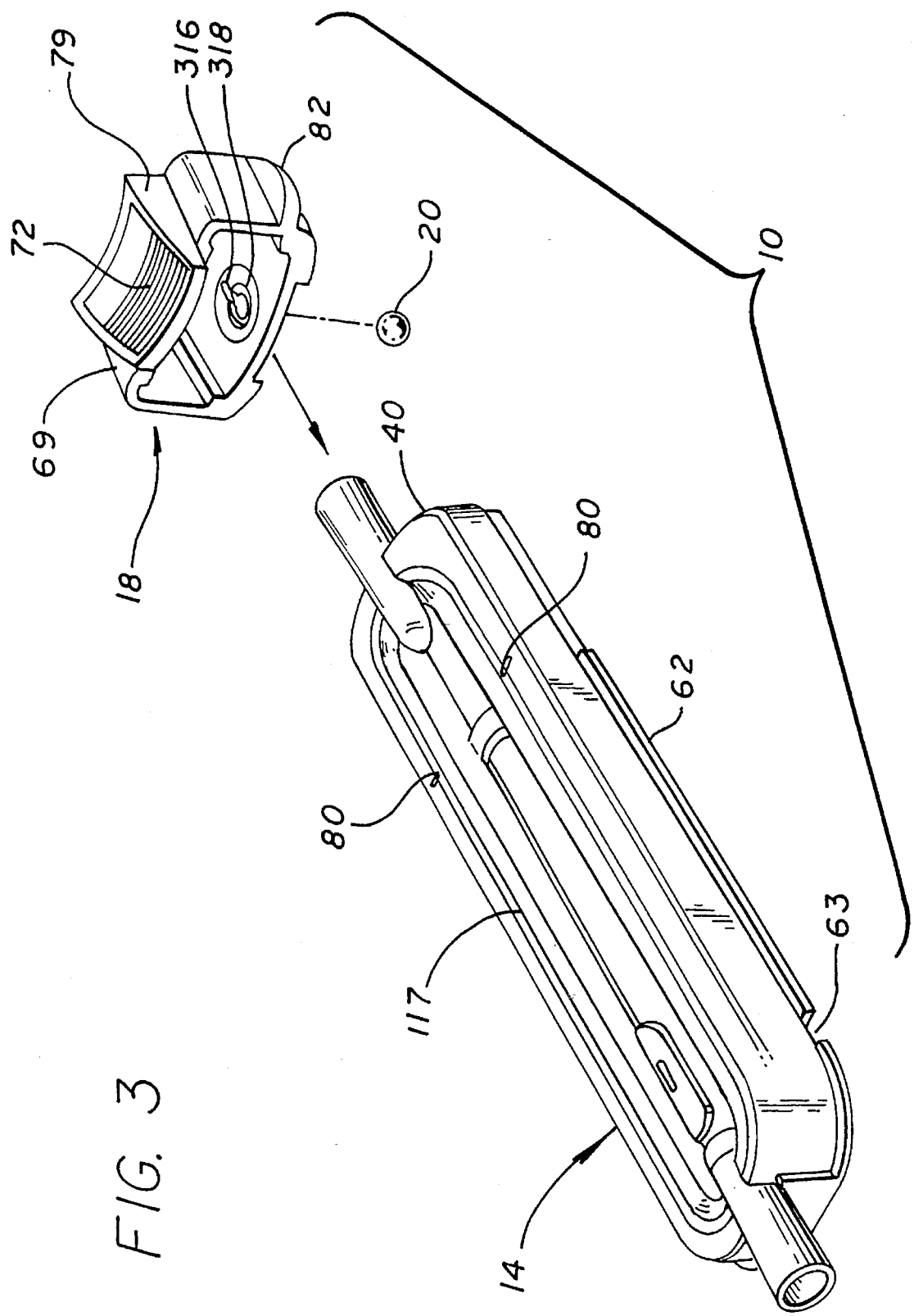
FIG. 3 is a partially assembled view of the engineered pumping segment shown in FIG. 1 showing the lower side and showing the slider distal to the segment.

As best seen in FIG. 3, the center portion of the second long side 69 includes a ramped projection 79 extending therefrom at an angle to the length of the slider 18. The ramped projection 79 has a concave shape well suited for receiving an operator's thumb. Formed in the concave-shaped ramped projection 79 are a plurality of parallel ridges 72 extending laterally across the ramped projection 79, which function to aid the operator in gripping the slider 18.

As seen in FIGS. 1, 2, 3, 7, and 13, the slider includes a strain relief notch 316 that tends to inhibit the socket 71 and slider 18 from breaking during assembly of the ball 20 through the socket. In a further feature shown in FIG. 7, the socket 71 includes a counter-bore 318 at its upper surface. This counter-bore facilitates assembly of the ball through the socket in that the ball must pass through less material now to reach its ultimate destination. The remaining slider material between the ball and the counter-bore is sufficient to withstand the pressures that may be experienced during operation Now that the details of the individual components of the pumping segment 10 have been described, their interaction and assembly will be addressed. Referring to FIG. 2, to assemble the pumping segment 10, the membrane 12 is placed within the base 14 with the flexible dome-shaped pressure vessel 36 pointing away from the interior 42 of the base 14 and overlaying the bubble ejector 64 of the base 14. Next, the cover 16 is placed within the base 14 so that the circular aperture 56 of the cover 16 fits around the dome-shaped pressure vessel and so that the interior 52 of the cover 16 faces the interior 42 of the base 14. As mentioned above, the projection 152 assists in centering the membrane in the cover.

Further, as may be appreciated from FIG. 3, once the membrane 12 is sandwiched between the base 14 and cover 16, the slider 18 may be placed about the base 14 and cover 16. The slider 18 is oriented so that its second long side 69 overlays the exterior 117 of the base 14 and so that the most elevated portion of the ramped projection 79 is positioned closest to the proximal end 40 of the pumping segment 10. Finally, to complete the assembly of the pumping segment 10, the ball 20 is pressed through the counter-bore 318 and the socket 71 to now be held in place between the socket 71 and the membrane. Because the ball is now between the slider and the membrane, it retains the slider on the assembled base when the slider is moved towards the proximal end of the segment 10 because the ball will encounter the end wall 81 of the cover and be prevented from moving further.

As shown in FIG. 5, in the preferred embodiment, the membrane 12 and base 14 form a sealed channel 22 for fluid flow. As stated above, the base 14 includes a groove 21 extending longitudinally along and substantially the length of the base 14. When the pumping segment 10 is assembled, the membrane 12 is placed between the base 14 and cover 16 with its upper and lower sidewalls 29, 30 sealingly seated within the membrane recess 46 of the base 14 and the membrane indentation 55 of the cover 16 respectively, and with its lower surface 27 overlaying the groove 21. When the pumping segment 10 is so assembled, space for fluid flow exists between the lower surface 27 of the membrane 12 and the groove 21 of the base 14 in the form a sealed channel 22. (It is to be noted that all further references to the structure of the pumping segment 10 and the components thereof, will be of an assembled pumping segment 10.)

Figure 14:
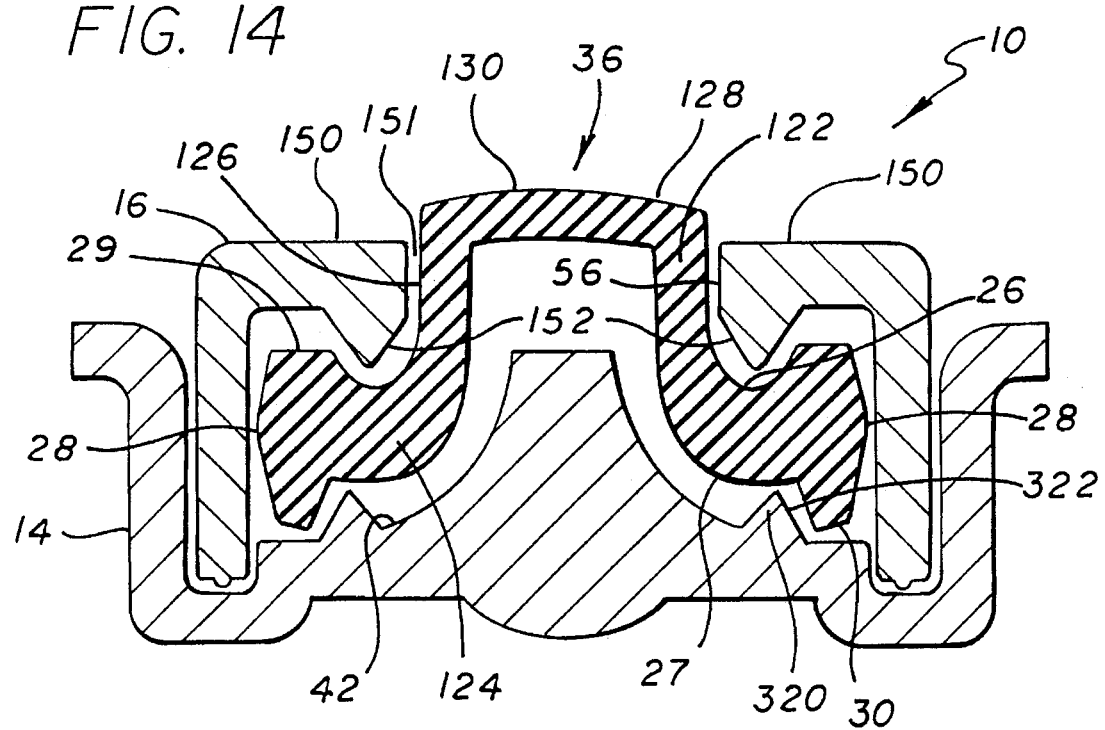
FIG. 14 is an enlarged cross-sectional view taken along line 14—14 of FIG. 1.
Figure 15:
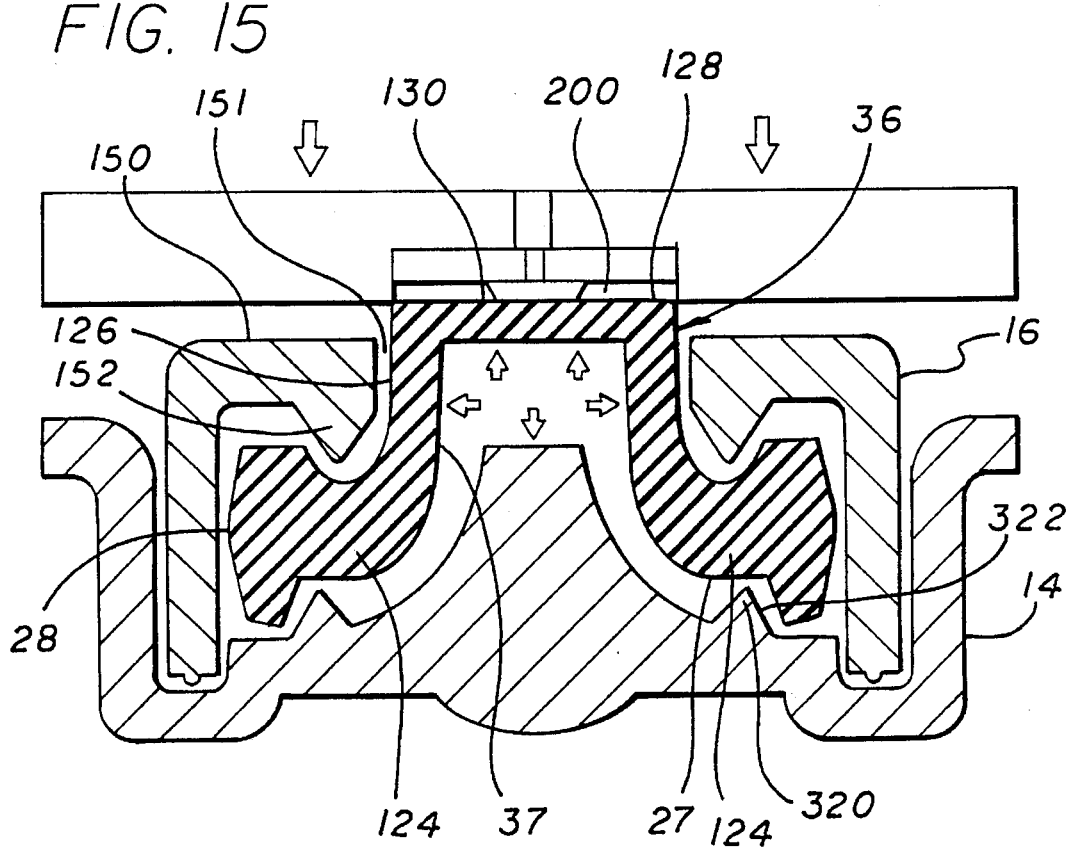
FIG. 15 is the cross-sectional view of FIG. 14, showing the engineered pumping segment coupled to a pressure sensor.

That channel is sealed by means of the configuration of the membrane edge and shapes of the base and cover that receive that membrane edge. Because of that configuration, a self-energizing seal is formed. Referring now to FIGS. 5, 14 and 15, the edge 28 of the membrane 12 is shown. In FIGS. 14 and 15, that edge in its relaxed configuration can be seen. In FIG. 5, the edge is compressed into its operational shape between the base 14 and cover 16. Although FIGS. 14 and 15 show the membrane assembled with the cover and base, the edge 28 is the membrane is not shown compressed for clarity of illustration only. The base 14 includes a raised seal member 320 having a slanted surface 322 for engaging the edge 28 of the membrane 12. The point of the seal member 320 interacting with the membrane provides a first seal to fluid in the groove 22. Should fluid pressure overcome the first seal, it would attempt to migrate between the slanted surface 322 and the membrane edge 28. However, the slanted surface 322 receives the force of the compressed edge 28 against it and operates as an O-ring seal prohibiting further leakage. For this reason, the seal is commonly referred to as a self-energizing seal.

Figure 8:
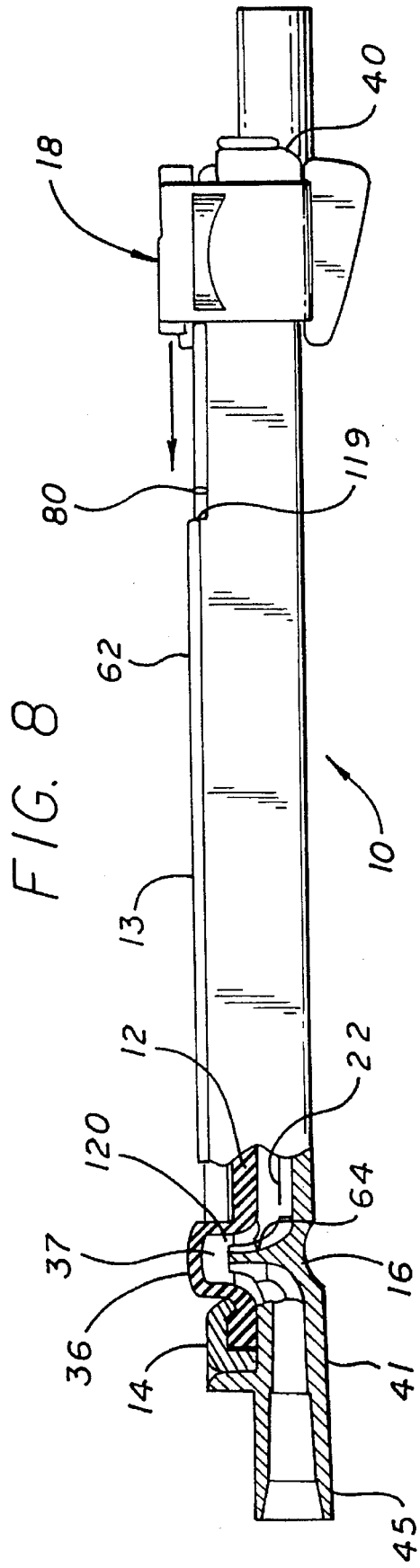
FIG. 8 is a side elevational view of the engineered pumping segment of FIG. 1, shown in partial cross-section.

The path for fluid flow through the assembled pumping segment 10 will be described next. Referring to FIG. 8, the tubing fitting 44 formed at the proximal end 40 of the pumping segment 10 defines the entrance to the pumping segment 10. Fluid entering the tubing fitting 44 first encounters the portion of the channel 22 defined by the fluid control region 59 formed in the groove 21 and the portion of the membrane 12 overlaying the control region 59. From there, fluid advances through the intermediate section 13 of the pumping segment 10.

Figure 9:
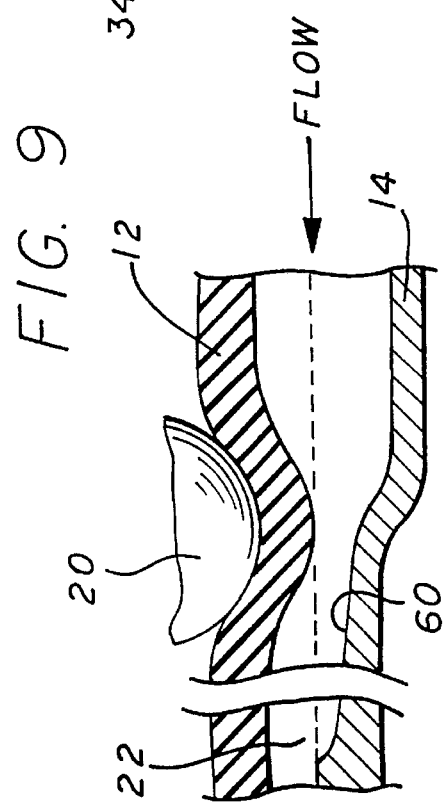
FIG. 9 is an enlarged fragmentary view of the cross-sectional view of FIG. 7.

Next, the interaction of the slider 18 with the other components of the pumping segment will be described. As previously stated, the slider 18 is adapted to longitudinally travel along the pumping segment 10 near its proximal end 40. Referring now also to FIG. 9, the longitudinal motion of the slider 18 toward the distal end 41 of the pumping segment 10 is limited by terminating ends 119 of the flange 62 of the base 14. Also, the slider 18 causes the click stops 80 and 314 (FIGS. 2 and 4) to engage as the slider 18 approaches the terminating ends 119 of the flange 62, causing an audible "clicking" and an identifiable feel, which indicate that the slider has been moved to the middle of the pumping segment 10 or to its most distal position, i.e., toward the distal end 41 of the pumping segment 10.

Figure 7:
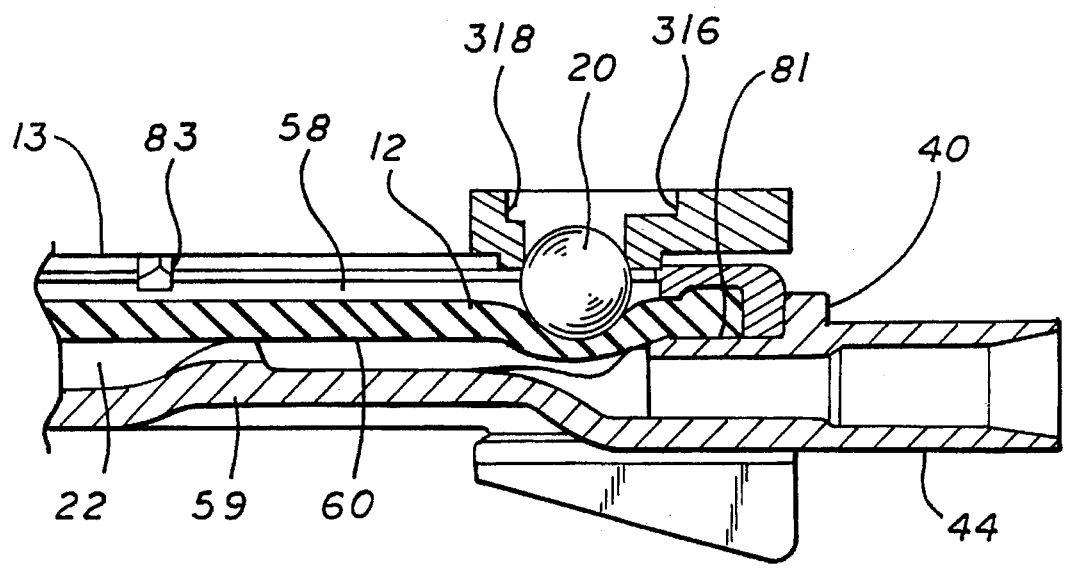
FIG. 7 is an enlarged fragmentary cross-sectional view of the flow regulation area of the segment showing the slider with ball in a proximal position.

As is shown in FIGS. 7 and 9, the ball 20 of the slider 18 is adapted to travel within the fluid regulation aperture 58 of the cover 16 and functions to depress the membrane 12 sealingly against the control region 59 of the base 14, thus preventing flow except through the variable cross-section groove 60 (see FIG. 6). Because the regulation section 59 has the approximate shape of the ball 20 and membrane compressed by the ball, fluid will not flow through the section except through the variable cross-section groove 60.

Thus, moving the ball along the regulation section 59 will expose more or less area of the groove thereby controlling the flow. Such movement functions to control the rate of fluid flow through the pumping segment 10. When the slider 18 is placed in its most distal position, the ball 20 depresses the membrane 12 against the portion of the regulation section 324 that has no groove thus completely stopping flow through the pumping segment 10. It is also to be noted that, in addition to the ends 119 of the flange 62 limiting the travel of the slider 18 in the distal direction, as the slider 18 is moved within the fluid regulation aperture 58, the longitudinal motion of the slider 18 along the pumping segment 10 in the proximal direction is also limited by the engagement of the ball 20 with longitudinally spaced apart end walls 81 and 83 of the fluid regulation aperture 58.

In another embodiment (not shown), the slider 18 has structure which substitutes for the ball 20 and functions to depress the membrane 12 against the base 14. For example, it is contemplated that the slider 18 may embody a projection having a predetermined width and extending a predetermined distance from the underside of the first side of the slider 18 so that a sufficient portion of the membrane 12 interacts with the control region 59 of the base to thereby control fluid flow.

The pumping segment shown in the figures and described herein provides increased accuracy in that only one portion is flexible; that is, the membrane. The remainder of the pumping portion of the segment is rigid. Specifically, the base 14 includes the pumping groove 21 that receives the peristaltic fingers of a pumping mechanism. Only a planar membrane 12 covers that pumping groove. The groove size can be more closely controlled during manufacture as can the dimensions of the planar membrane. These features provide advantages over prior systems that operate on cylindrical tubing as the fluid conduit. The dimensions of such tubing can vary significantly from manufacturer to manufacturer and the tubing tends to deform after use.

Combining the base and membrane with the slider for flow control also enhances accuracy. The slider also operates with a rigid portion, the variable cross-sectional area groove 60. As with the pumping section, only the planar membrane 12 overlies the groove 60. Because more of the flow control section is formed of rigid components, increased accuracy can be obtained during manufacture. This flow control configuration thus provides advantages over prior systems than operated on cylindrical tubing.

Figure 10:
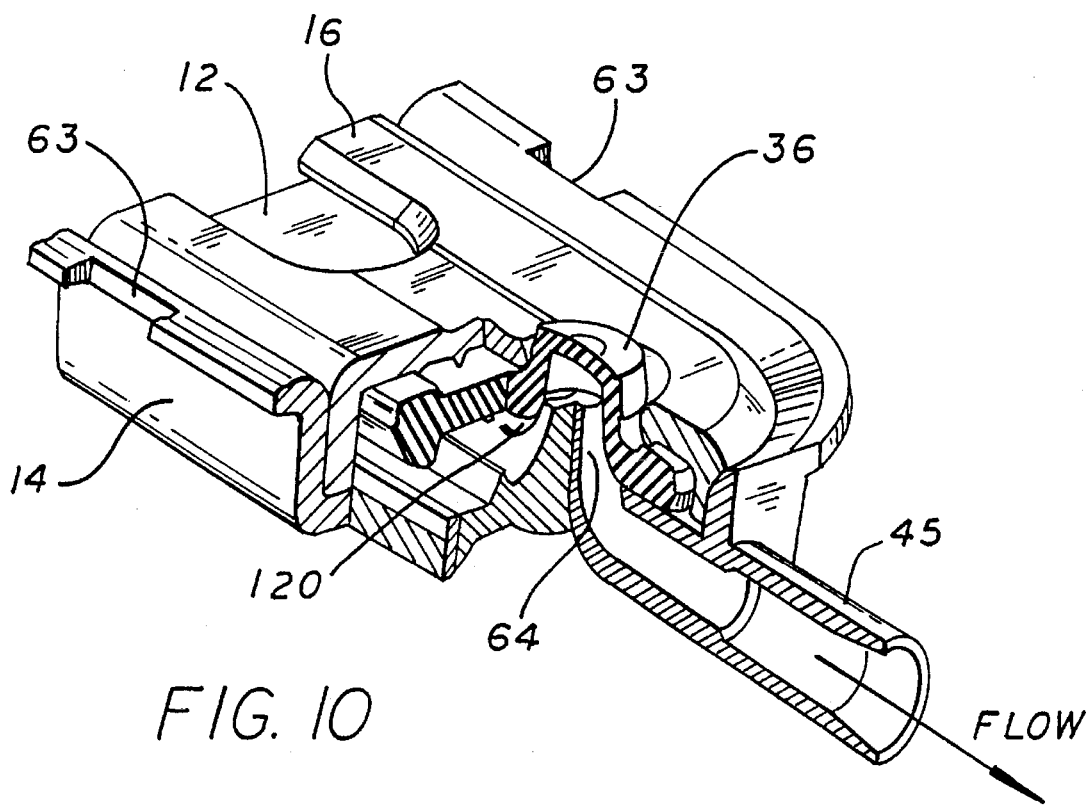
FIG. 10 is a partial cross-sectional view of the air ejection portion of the pumping segment.
Figure 11:
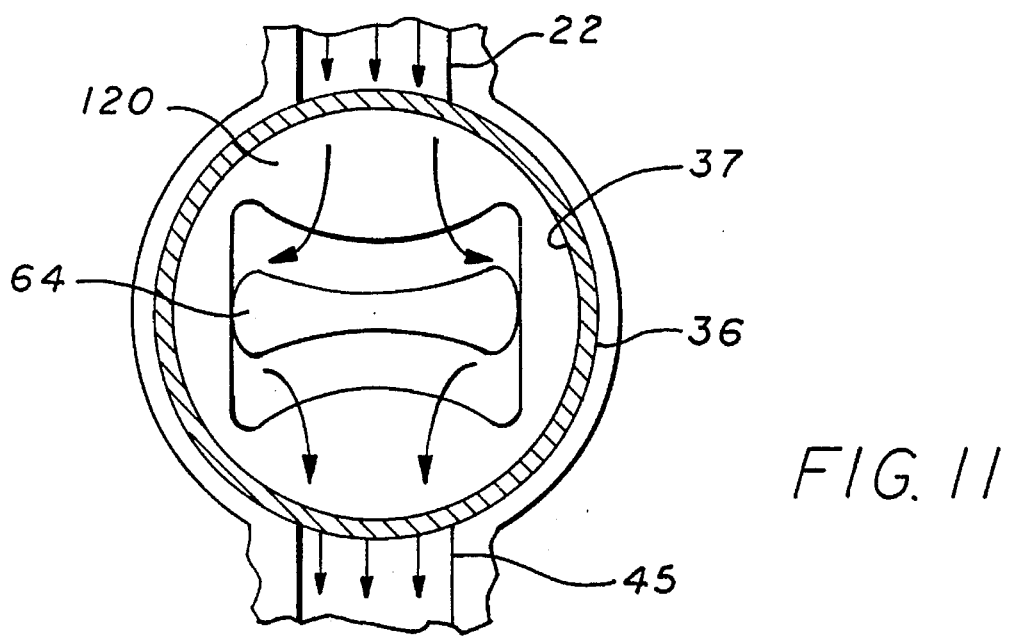
FIG. 11 is a top view of the air ejection apparatus of FIG. 10.

As shown in FIGS. 8, 10 and 11, fluid encounters a runnel 120 which is that portion of the channel 22 formed by the bubble ejector 64 projecting from the base 14 and the dome-shaped pressure vessel 36 formed in the membrane 12. The dome-shaped pressure vessel 36 is mounted so that it receives the fluid of the conduit but is not in the direct flow path of that fluid. Therefore, air bubbles in the conduit may collect in the pressure vessel due to the lack of flow to wash them out. The air bubble ejection system redirects the flow of the fluid through the conduit so that it proceeds through the vessel 36 to wash out any air bubbles that may enter the vessel. Generally speaking, the bubble ejector 64 cooperates with the interior 37 of the pressure vessel 36 to eliminate dead space and to inhibit the production of bubbles in fluid that is caused to flow through the runnel 120. Thus, the accumulation of compressible air bubbles in the pressure sensing vessel is inhibited and accuracy is improved. Because air is compressible, the accuracy of a pressure reading taken from the vessel having air bubbles within it may be compromised. The fluid passes through the runnel 120 and then exits the pumping segment 10 through the tubing fitting 45 formed at the distal end 41 of the base 14.

The vane 64 is positioned in the conduit under the vessel 36 to guide the flow of the fluid from the conduit into the vessel so that the vessel now lies directly in the flow path of fluid through the conduit. The redirected fluid washes the vessel 36 of any air bubbles that may have accumulated there. The vane is shaped so that the redirected fluid from the conduit reaches all parts of the vessel to remove any bubbles. In the embodiments shown, the vane 64 has the appearance of an hour glass with the edges rounded. It has been found that this shape causes fluid flowing at the vane 64 to be directed upward into the interior 37 of the vessel where it reaches all parts of the vessel before flowing down the distal side of the vane and out the exit fitting 45.

In the embodiment shown, the vane is disposed at a right angle to the conduit 22 and has a size that varies according to its height so that the flow path across the vane and through the interior 37 of the vessel 36 has an approximately constant cross-sectional area. The height is selected to result in the approximately constant cross section flow area through the runnel 120 when the dome 36 is deformed inwardly during standard preload installation in a pressure sensor. Such deformation is shown in FIG. 15 and is described in detail below.

As best observed to FIG. 10, the vane 64 of the bubble ejector is aligned with the central axis of the vessel 36. Furthermore, the vane 64 is shaped to provide for gradual and non-abrupt fluid flow transitions while still maintaining a uniform flow passage area 120. The flow area transitions are defined by substantially smooth curved surfaces extending over approximately ninety degrees across the direction of fluid flow. Fillets have been added in order to smooth out the angle of curvature and to provide for the gradual and non-abrupt transitions. Gradual transitions are provided to result in more controlled fluid flow and to reduce the amount of turbulence generated.

Referring particularly to FIG. 11, the vane 64 does not completely span the width of the conduit 22 and some flow will occur around the vane. However, a sufficient amount of flow is directed upward into the interior 37 of the vessel to wash out bubbles.

In a preferred embodiment, the bubble ejector 64 is formed of the same material and as an integral part of the engineered pumping segment base 14. However, it will be appreciated by those skilled in the art that other materials and methods of manufacture may be used.

Referring now to FIG. 14, attention is directed toward the cooperation of the dome-shaped pressure vessel 36 of the membrane 12 and the cover 16. In the preferred embodiment of the pumping segment 10, the cover 16 includes structure functioning as a lateral restraint 150. The lateral restraint 150 surrounds and supports the dome-shaped pressure vessel 36 when there are internal pressures existing in the pressure vessel 36 and the pressure vessel 36 is not coupled to a sensor.

When coupled to the pressure sensor, the sensor provides substantial structural support to the pressure dome giving it the capability to withstand very high internal fluid pressures. However, when the pumping segment is uncoupled from the pump, the pressure dome does not have the structural support of the sensor. The dome in this "free" state must carry the entire dome internal pressure loading. The dome must maintain structural integrity and not bulge or rupture under these conditions.

It has been found that by only limiting the lateral displacement of the dome side wall region, a significant gain in resistance of the entire dome region to bulge and rupture under high pressure can be achieved. By providing a limited clearance between the dome side wall and the lateral restraint feature in the cover, the lateral deflection of the dome side wall region is not inhibited from responding to normal fluid pressures but is prevented from rupturing when experiencing high fluid pressures. Thus, the linearity performance of pressure sensing will not be impacted with fluid pressures in the normal operating range.

Essentially, the lateral restraint 150 includes that portion of the cover 16 that forms the circular aperture 56 surrounding the dome-shaped pressure vessel 36 that can also be observed in FIG. 2. A lateral clearance 151, for example 12 mils, exists between the cylindrical sidewall 126 (shown in cross-section in FIG. 11) of the dome-shaped vessel 36 and the lateral restraint 150. Also, the lateral restraint 150 includes a projection 152 extending from the lateral restraint 150 and directed towards the interior 42 of the base 14. The lateral restraint projection 152 also surrounds the pressure vessel 36. The projection 152 includes a 45° chamfer formed on the end thereof which extends away from and which aids in supporting the dome-shaped pressure vessel 36. The chamfer avoids interference with the normal operation of the pressure vessel by the lateral restraint 150 yet continues to provide a sufficient amount of material for use as the lateral restraint.

In use, as shown in FIG. 12, the pumping segment 10 is placed within an elongate receiving cavity 199 of a peristaltic pumping system 300 that operates to peristaltically pump fluids through the pumping segment 10 as well as control fluid flow and measure fluid line pressure. The varied outer shape of the segment 10 assists in proper loading of the segment. Because it is rounded at one end and flat at the other, it can be installed in only one orientation. Additionally, as better seen in FIG. 13, the rectangular notches 63 in the flange 62 of the pumping segment 10 cooperate with lateral tabs 263 in the receiving cavity 199. The lateral tabs 263 have a configuration that is adapted to mate with the rectangular notches 63 and assure that the pumping segment 10 is properly placed in the receiving cavity 199.

The pumping segment 10 also includes flats for assistance in proper mounting in the receiving cavity 199. A proximal flat 326 meets with a shoulder 328 in the cavity to aid in alignment. A distal flat 330 also meets a distal shoulder 332 in the cavity 199. These flats/shoulder combinations control the distance that the pumping segment can be inserted into the cavity 199.

Figure 13:
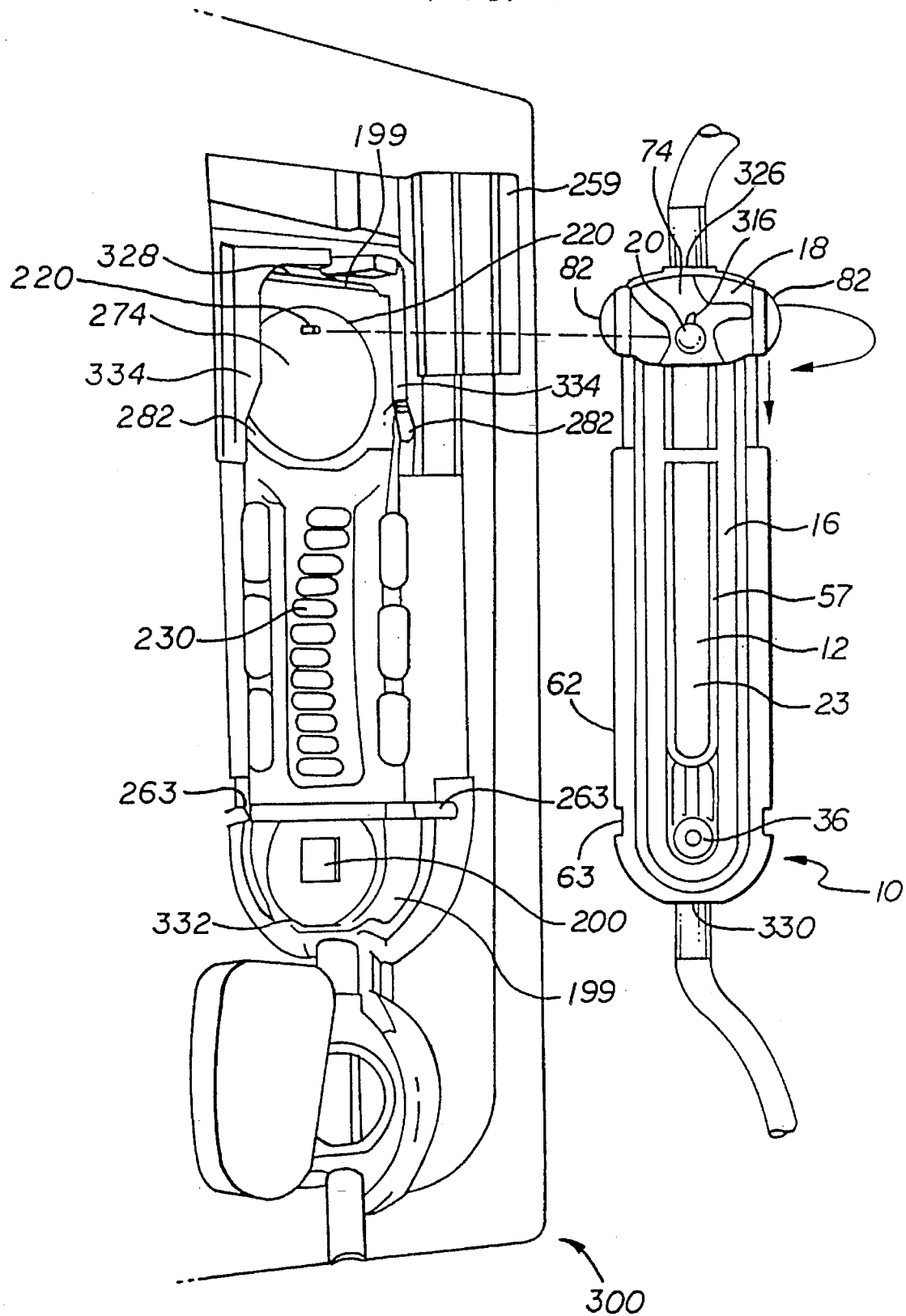
FIG. 13 is an enlarged fragmentary view of FIG. 12, showing the engineered pumping segment and the corresponding portion of the infusion system.

Further, rounded cut-outs 282 similarly cooperate and mate with the ears 82 extending from the slider 18 of the pumping segment 10 to assure that the pumping segment 10 is placed in the pumping system 300 with its slider 18 in the flow stop position although in FIG. 13 the slider 18 is shown in its full flow position. Thus, the slider 18 must be moved to its most distal or its fluid stop position before the pumping segment 10 can be placed in the receiving cavity 199 because it is only in this position that the ears 82 are received within the rounded cut-outs 282. With the slider 18 in its flow stop position, one or more pump/slider projections 220 extending perpendicularly from a rotatable circular plate 274 included in the elongate receiving cavity 199 of the peristaltic pumping system 300 are positioned within the groove 74 formed in the slider 18. A latch arm 259 of the peristaltic pumping system 300, which is mechanically connected to the rotatable circular plate 274, is closed to retain the pumping segment 10 in the pumping system 300. As the latch arm 259 is closed, the rotatable circular plate 274 turns and motion is translated from the rotatable circular plate 274 to the groove 74 to cause the slider 18 to move to its most proximal position along the engineered pumping segment 10. At this position, the maximal contemplated flow is permitted except where the pumping segment is installed in a pump, in which case, one or more peristaltic fingers will occlude the flow path downstream. When the slider is moved in the proximal direction, the ears 82 move under ridges 334 located on either side of the cavity 199. The ridges 334 retain the slider 18 and so the pumping segment in the cavity 199 so that it cannot be removed unless the slider is moved to its flow stop position.

Once the engineered pumping segment 10 is positioned within the peristaltic pumping system 300, peristaltic pumping fingers 230 projecting substantially perpendicularly from the elongate receiving cavity 199 may work within the intermediate aperture 57 formed in the cover 16 and upon the central planar region 23 of the membrane 12 overlaying the groove 21. The peristaltic pumping fingers 230 systematically rise and fall in a perpendicular motion relative to the membrane 12 and depress adjacent portions of the membrane 12 against the groove 21, to thereby force fluid through the engineered pumping segment 10.

Pressure sensing is also accomplished when the engineered pumping segment 10 has been placed in the peristaltic pumping system 300. In order to accomplish pressure sensing, the dome-shaped pressure vessel 36 is brought into continuous and direct contact with a pressure sensitive region of a sensor 200 mounted within the elongate receiving cavity 199 to form an effective interface for sensing pressures created by fluid flowing through the engineered pumping segment 10.

As shown in FIG. 15, in the preferred embodiment, the pressure vessel 36 is coupled to an essentially planar sensor 200 so that fluid pressure readings may be taken of fluid flowing through an interior 37 of the vessel 36. The structural configuration of the pressure vessel 36 is selected to ensure optimum interfacing with the sensor 200, as will be described in detail below. In general, an optimum initial top contour of the pressure vessel 36 is achieved by employing a novel method. Additionally, another novel method is used to optimize sensor/dome preload displacement. By preloading an optimally shaped pressure vessel 36 against the pressure sensitive region of a sensor with optimal preload displacement, proper interface contact stress with the sensor 200 is assured, thereby ensuring pressure communication from the vessel 36 to the sensor even in situations where there is negative pressure existing in the pumping segment 10.

Referring again to FIG. 14, the detailed configuration of the dome-shaped pressure vessel 36 is described. In the preferred embodiment, the dome-shaped pressure vessel 36 has a crown 122 and a membrane peripheral region 124 which connects the crown 122 to the perimeter 28 and planar portion of the membrane 12. The crown 122 has cylindrical sidewalls 126 which extend substantially perpendicular from the planar portions of the membrane and which define an outer rim region 128. The outer rim region 128 is defined by the top of the cylindrical sidewalls 126 and is itself circular in shape. Completing the crown 122 is a center dome region 130. The center dome region 130 is the cap of the vessel 36 or that portion of the vessel that closes one end of the cylindrical sidewalls 126. From its connection to the sidewalls 126, the center dome region 130 has an arcuate surface contour that gradually extends further away from the planar portions of the membrane 12 and forms a dome-like shape.

The membrane peripheral region 124 is a curved portion of the membrane 12 extending away from the sidewalls 126 to provide a transition to the upper and lower sidewalls 29, 30 formed at the distal terminal end 25 of the membrane as well as a transition to the central planar region 23 (not shown in FIG. 14) extending toward the proximal terminal end 26 of the membrane. The membrane peripheral region 124 functions as a flat washer spring. As will be developed, the membrane peripheral region 124 provides resilient stiffness while allowing the central dome region 130 to be flattened and the rim region 128 to be preloaded against the sensor 200.

It is also contemplated that the crown height, thickness and modulus of elasticity will be selected to provide acceptable pressure transferring characteristics. Likewise, the sidewall 126 thickness and modulus of elasticity as well as that of the membrane peripheral region 124 will be selected with such characteristics in mind. In particular, the physical characteristics of the membrane peripheral region 124 may be chosen to prevent dome/sensor lift-off under conditions of negative IV fluid pressure. Additionally, the diameter of the central dome region 130 is contemplated to be more than twice that of the largest dimension of the sensing portion 231 of the pressure sensor 200, thereby minimizing the effect of lateral position errors on sensor accuracy.

In the preferred embodiment, the wall thickness of the crown 122 and center dome region 130 range from 0.033–0.035 inches. The radius of the crown portion from the outside of the sidewalls 126 to a longitudinal axis running through the crown is 0.107–0.109 inches. The height of the cylindrical sidewalls 126 from a point near where the membrane peripheral region 124 meets the upper sidewall 29 is 0.105–0.107 inches. The curvature of the upper side 26 of the membrane peripheral region 124 where it meets the cylindrical sidewalls 126 has a radius of approximately 0.032 inches, whereas the curvature of the lower side 27 has a radius of approximately 0.072 inches. Accordingly, the wall thickness of the membrane peripheral region 124 increases from 0.038–0.040 inches to approximately 0.065 inches. The center dome region 130 gradually inclines to a height of 0.011–0.013 inches above the outer rim region 128. A description of a preferred center dome region 130 contour in terms of radial position and height above the outer rim region 128 is summarized below.

| RADIUS (inch) | HEIGHT (inch) |
| --- | --- |
| 0.0000 | 0.01200 |
| 0.0024 | 0.011979 |
| 0.0048 | 0.011952 |
| 0.0072 | 0.011883 |
| 0.0096 | 0.011801 |
| 0.0120 | 0.011683 |
| 0.0144 | 0.01155 |
| 0.0168 | 0.011376 |
| 0.0192 | 0.011175 |
| 0.0216 | 0.010961 |
| 0.0240 | 0.010715 |
| 0.0264 | 0.010448 |
| 0.0288 | 0.010151 |
| 0.0312 | 0.009835 |
| 0.0336 | 0.009487 |
| 0.0360 | 0.009133 |
| 0.0384 | 0.008761 |
| 0.0408 | 0.008351 |
| 0.0432 | 0.007919 |
| 0.0456 | 0.007483 |
| 0.0480 | 0.007028 |
| 0.0504 | 0.006543 |
| 0.0528 | 0.006053 |
| 0.0552 | 0.005556 |

-continued

| RADIUS (inch) | HEIGHT (inch) |
| --- | --- |
| 0.0576 | 0.005078 |
| 0.0600 | 0.004606 |
| 0.0624 | 0.004188 |
| 0.0648 | 0.003769 |
| 0.0672 | 0.003489 |
| 0.0696 | 0.003274 |
| 0.0720 | 0.0003076 |
| 0.0744 | 0.002875 |
| 0.0768 | 0.002631 |
| 0.0792 | 0.002363 |
| 0.0816 | 0.002103 |
| 0.0840 | 0.001882 |
| 0.0864 | 0.001697 |
| 0.0888 | 0.001419 |
| 0.0912 | 0.001293 |
| 0.0936 | 0.001125 |
| 0.0960 | 0.000952 |
| 0.0984 | 0.000789 |
| 0.1008 | 0.000613 |
| 0.1032 | 0.000352 |
| 0.1056 | 0.000133 |
| 0.1080 | 0.0 |

The dome-shaped pressure vessel 36 has an uncoupled initial top surface contour such that, upon coupling to a sensor face, relatively uniform central dome region contact stress distribution will result at the interface between the sensor 200 and the dome 130 for any given internal fluid pressure. By approximating a uniform contact stress distribution, a more accurate transfer of fluid pressure information from the dome 130 to the sensor 200 is achieved since the entire dome portion 130 is presenting the sensor 200 with the same information. This feature compensates for various manufacturing tolerances. For example, if the pressure sensor were to be mounted in a position displaced from its design position during manufacture of a pump, the chances of the pressure sensing system functioning accurately are increased due to the uniform contact stress distribution provided by the vessel. Likewise, the pressure vessel may be mounted to the pressure sensor in a displaced position from the design position and still function accurately because of the uniform contact stress distribution provided by the dome-shaped contour of the vessel.

In order to determine a proper initial contour, a preferred embodiment of which is provided in the table above, a novel method for providing the dome-shaped pressure vessel 36 with an optimal top contour is employed. The following is a description of this method.

To determine an optimal top contour (see FIG. 16), it will be appreciated that a first uniform contact stress $P_r$ 134 (represented by arrows) and a second uniform contact stress $P_c$ 136 (represented by arrows) are applied to the rim region 128 and the center dome region 130 respectively. Uniform contact stresses $P_r$ 134 and $P_c$ 136 simulate the forces applied to the dome-shaped pressure vessel 36 upon coupling with a sensor 200. Stresses $P_r$ 134 and $P_c$ 136 are necessarily different due to differences in the stiffness or rigidity of the rim 128 and center dome 130 regions and, $P_r$ 134 is substantially greater because of the greater rigidity of the rim 128. Further, it is important that the stresses be uniform, especially for the central dome stress $P_c$ 136, because it is desired to contact the sensor 200 with a uniform stress distribution. Upon the application of sufficient stresses or upon coupling to the sensor 200, the top portion of the dome-shaped pressure vessel 36 is to be substantially flattened against the sensor face. It is to be understood that merely coupling a deformable irregular shaped surface against a flat sensor surface so as to flatten the irregularly shaped surface, does not necessarily result in a uniform stress distribution across the deformable irregular shaped surface. Such a shaped surface likely has areas of varied stress distribution across its flattened surface since it would likely require various stresses to flatten different areas of the surface. Additionally, coupling a flat surface, supported by sidewalls projecting perpendicularly therefrom, against a flat sensor surface will likely result in the sections of the flat surface near the sidewalls having a different distribution stress than that of the center portion of the flat surface. Accordingly, the method of optimizing the initial top surface contour of the dome-shaped pressure vessel 36 results in providing the engineered pumping segment 10 with superior means to transfer pressure information to a sensor.

To establish the optimum top contour, an initial contour $h(d_c, d_r)$ 140 (represented by the connected points in FIG. 16) is selected, where $d_c$ 142 and $d_r$ 144 (both depicted as arrows in FIG. 16) represent the deflection coordinates of the dome center 130 and dome rim 128 respectively. In this method, $y(d_c,d_r)$ 141 represents the absolute displacement response of $h(d_c,d_r)$ 140 to the application of uniform stresses $P_r$ 134 and $P_c$ 136. To understand the relationship between $y(d_c,d_r)$ 141 and $h(d_c,d_r)$ 140, one must conceptually replot $h(d_c,d_r)$ 140 as a straight line 143, where both $d_c$ 142 and $d_r$ 141 equal zero, and visualize displacement response $y(d_c,d_r)$ 141 as an expression of the changes in deflection coordinates $d_c$ 142 and $d_r$ 144 to applied stresses. It is desired that, in response to applied stresses, the initial contour $h(d_c,d_r)$ 140 equal the relative displacement response $y(d_c,d_r)$ 652 so that the center dome region 130 is substantially flattened. After observing a relative response $y(d_c,d_r)$ 141 (represented by arrows in FIG. 16) of the top portion to uniform stresses $P_r$ 134 and $P_c$ 136, it may be required to determine a revised contour $h(d_c,d_r)'$. That is, revised initial contour $h(d_c,d_r)'$ may be necessary where $y(d_c,d_r)$ 141 is not the desired relative response of the top portion of the pressure vessel to applied uniform stresses $P_r$ 134 and $P_c$ 136. Once $h(d_c,d_r)$ 140, or more precisely some revised estimation $h(d_c,d_r)'$ of $h(d_c,d_r)$ 140, equals $y(d_c,d_r)$ 652, the optimal contour of the top portion of the vessel 36 has been achieved.

Upon coupling to sensor 200 or through the application of uniform contact stresses $P_r$ 134 and $P_c$ 136, the optimally shaped top portion will deflect sufficiently to flatten the central dome region 130 (see FIG. 15). Further, the membrane peripheral region 124, in performing as a flat washer spring, deforms an amount corresponding to the deflection of the rim region 128, thereby absorbing the forces applied to the rim region 128 and enabling the sidewalls 126 to remain substantially straight. Generally speaking, in an optimally shaped dome-shaped pressure vessel 36, where the central dome region 130 is sufficiently flattened in response to uniform stresses, relatively uniform stress distribution exists across the center dome region 130. Therefore, upon coupling, the dome 130 transfers a uniform and accurate pressure to the sensing portion 131 of the sensor 200.

To increase accuracy, it is desirable to provide a pressure vessel that interfaces with a pressure sensor such that the contact stresses between the vessel and sensor are linear across the entire design range of internal pressures of the vessel. The present invention also includes a method to optimize the preload displacement of the dome-shaped pressure vessel 36 so that, when coupled to the sensor 200 (see FIGS. 15 and 16), the rim region 128 isolates the central dome region 130 from external conditions and so that a proper interface exists for all expected mechanical tolerance deviations and for worst case negative pressure conditions, i.e., −4 psi. To arrive at an optimum preload displacement, an initial nominal preload displacement under conditions of zero internal pressure is assumed and the resulting stresses between the rim and central dome regions 128, 130 and the sensor 200 are determined for the worst case negative pressure conditions expected. If sufficiently positive compressive resulting stresses are computed, then the assumed nominal preload displacement is deemed optimized. On the other hand, if the resulting stresses are not sufficiently positive, a new assumption for the initial nominal displacement is made and the resulting stresses are again monitored for sufficiency. In order to obtain other assumptions for initial nominal displacement, it may be necessary to modify the membrane stiffness by adding material or by changing its composition.

To accomplish optimal preload displacement for all expected internal fluid pressures, an initial preload displacement is selected for the rim region 130 and center dome region 128 under zero internal pressure conditions. The stresses existing in the rim and center dome regions are then determined for this initial preload displacement. Next, an expression is developed which represents the relationship between resulting contact stresses $P_c$ 134 and $P_r$ 136 for all expected internal pressures and, contact stress values for zero internal pressure $P_{co}$ and $P_{ro}$ and pressure transfer coefficients $C_c$ and $C_r$. Finally, the resulting stresses are evaluated for sufficiency.

Stress values $P_{co}$ and $P_{ro}$ are initially approximated from the following equations which represent linear estimations of central dome 130 and rim region 128 stresses under conditions of zero internal pressure for small displacement deviations $d_c$, $d_r$, from nominal.

$$P_{co} = P_{co,nom} + (dP_{co}/dd_c) \times (d_c - d_{c,nom})$$

$$P_{ro} = P_{ro,nom} + (dP_{ro}/dd_r) \times (d_r - d_{r,nom})$$

In the above two equations, the assumed initial nominal preload deflections, $d_{c,nom}$ and $d_{r,nom}$, under zero internal pressure conditions, are known. They are determined by knowing the optimal initial top surface contour, as arrived at using the method described above, and by observing the change in the optimal initial top surface contour upon coupling to the sensor 200 to the assumed degree. For such assumed initial nominal preload deflection, there are known associated nominal central dome and rim stresses $P_{co,nom}$ and $P_{ro,nom}$. Due to mechanical tolerance deviations, however, the actual contact stresses between the dome-shaped pressure vessel 36 and the sensor 200, $P_{co}$ and $P_{ro}$, will not equal the nominal values. The above equations are utilized to take into account small displacement deviations from nominal that are likely to occur in the contact stresses of the rim region $P_{ro}$ and central dome region $P_{co}$ under zero internal pressure conditions. This is accomplished by adding to the nominal contact stress values the effect small deviations in displacement from nominal have on the contact stress values. The actual central dome region and rim region contact stresses, $P_{co}$ and $P_{ro}$, are then calculated for some displacement deviations, $d_c$ and $d_r$, from nominal which are representative of expected deviations and for some associated known change in actual central dome and rim contact stresses with respect to the expected deviations in central dome and rim displacements, $dP_{co}/dd_c$ and $dP_{ro}/dd_r$. It is to be noted that $dP_{co}/dd_c$ and $dP_{ro}/dd_r$ are known by observing the change in central dome and rim region contact stress under zero internal conditions for various displacements of the central dome and rim regions 130, 128. Therefore, what is arrived at is a more realistic and better approximation of the actual contact stresses under zero internal pressure conditions.

Once $P_{co}$ and $P_{ro}$ are estimated, they are utilized to calculate resulting contact stresses $P_r$ 134 and $P_c$ 136 for each expected internal vessel pressure $P_{int}$ from following relationships.

$$P_c = P_{co} + C_c \times P_{int}$$

$$P_r = P_{ro} + C_r \times P_{int}$$

In order to make such a calculation, pressure transfer coefficients $C_c$ and $C_r$ are estimated, based upon the response of the vessel 36 to the application of stresses $P_r$ 134 and $P_c$ 136, using a finite element stress analysis, for example the finite element stress analysis program from MARC Analysis Research Corporation, Palo Alto, Calif., for a given preload displacement. For any internal pressure $P_{int}$, therefore, $P_c$ 136 and $P_r$ 134 may be determined.

Where sufficiently positive compressive contact stresses $P_c$ 136 and $P_r$ 134 are computed, that is, through the application of the contact stresses the central dome region 130 is sufficiently isolated by the rim region 128 under expected worst case negative pressure conditions, then the assumed displacement of the pressure vessel 36 utilized in the analysis is optimal. Otherwise, the dome adjacent region membrane may be increased in thickness (or stiffened) and a larger preload displacement value utilized. In such a case, the complete optimization analysis described would then be again performed using the new assumptions with the stresses $P_c$ and $P_r$ again being monitored for adequacy.

It must be noted that the previously described optimal contour and optimal preload displacement methods are dependent upon the specific application and physical characteristics of the subject pressure transferring element. Although different applications will have varying results, the method outlined will provide means for optimizing the performance of a pressure transferring element.

Our attention is now turned to another basic function of the pumping segment 10, namely fluid flow regulation. Briefly, referring to FIG. 13, to regulate flow rates through the pumping segment 10, the pumping segment 10 must be removed from the pumping system 300 and the slider 18 must be manipulated by hand. As may be recalled, when the latch arm 259 is closed to retain the pumping segment 10 within the pumping system 300, the slider 18 is moved to its most proximal position where fluid flow through the pumping segment 10 is its maximum. Further, it may be recalled that to place the slider 18 within the pumping system 300, the slider 18 must be in its most distal or its flow stop position, only later to be moved to its maximum flow position when the latch arm 259 is closed. Therefore, since the position of the slider 18 is constrained to be in its maximum flow position when it is retained against the pumping system 300, the slider 18 must be removed from the pumping system 300 and manipulated by hand should flow regulation be desired. Under such conditions, gravity causes the fluid coming from the reservoir (not shown) to pass through the pumping segment 10, the rate of fluid flow through which is determined by the slider 18.

Figure 17:
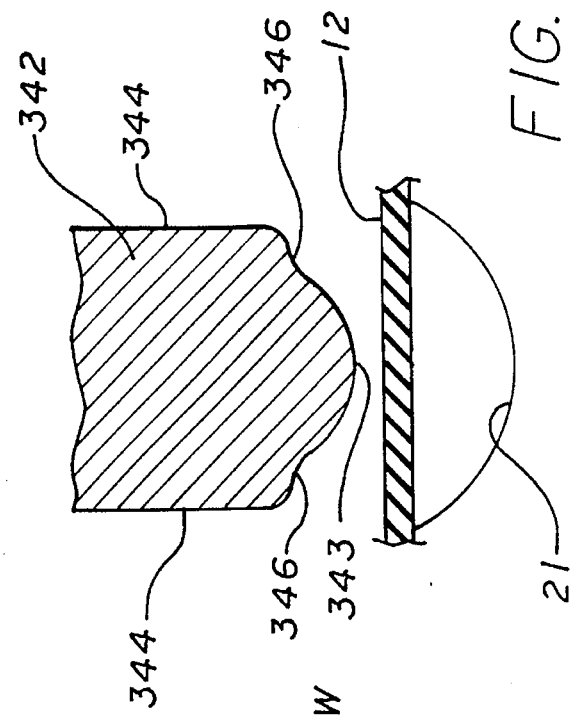
FIG. 17 is a side view of a pumping mechanism peristaltic finger usable with the membrane and groove shown in FIG. 5.

Referring now to FIG. 17, the shape of a peristaltic finger 342 is shown that is usable with the pumping segment 10 presented. As shown, the finger 342 has a complex curve at its distal end for compressing the membrane 12. While the tip comprises a convex curve, the parts of the finger tip between the center and the edges 344 comprise concave curves. It was found that this shape of the finger 342 results in less wear on the membrane during the pumping action.

From the foregoing, it will be appreciated that the present invention provides an engineered pumping segment 10 having a simple design and that in a single device facilitates efficient and accurate peristaltic pumping of fluid over long periods of time, that provides an effective interface for sensing fluid pressure under all conditions of line pressure, and that provides regulation of fluid flow while minimizing system inaccuracies.

While several particular forms of the invention have been illustrated and described, it will be apparent that various modifications can be made without departing from the spirit and scope of the invention. Accordingly, it is not intended that the invention be limited, except as by the appended claims.

We claim:

1. A fluid conducting segment for use with a fluid pump that acts on the segment for controlled fluid flow to a patient, the segment comprising:
   a rigid body portion having:
   a pumping portion;
   a fluid regulation portion;
   a pressure sensor interfacing portion;
   an input port; and
   an output port;
   wherein said input and output ports are disposed in said rigid body portion so that they oppose each other.

2. The segment of claim 1, further comprising a slider that engages said fluid regulation portion to control flow through the segment.

3. The segment of claim 2, wherein said slider is positionable in a flow position and in a flow stop position.

4. The segment of claim 3, wherein said slider accomplishes variable flow control by being positioned at different points along the fluid regulation portion.

5. The segment of claim 4, wherein said fluid regulation portion includes click stops that operate with the slider to indicate that said slider is in a flow stop position.

6. The segment of claim 2, wherein said slider is configured to longitudinally travel along a portion of said body.

7. The segment of claim 3, wherein said slider includes engaging means for cooperating with the pump such that the pump positions said slider to be in the flow position during pumping.

8. The segment of claim 2, wherein said slider includes ears for restraining said slider within the fluid pump.

9. The segment of claim 1, wherein said body includes a perimeter and a flange projecting substantially perpendicularly from said perimeter, said flange having notches formed therein that facilitate proper positioning of the segment into the fluid pump.

10. The segment of claim 1, wherein said body includes a base, a membrane and a cover, said membrane being disposed between said cover and said base, said membrane being made from a resilient elastomeric material and having a sidewall projecting substantially perpendicularly around a perimeter thereof, said sidewall configured to form a self-energizing seal with said base and said cover.

11. The segment of claim 10, wherein said base includes a fluid control region and a groove formed in said fluid control region, wherein said membrane overlays said groove and said fluid control region.

12. The segment of claim 1, wherein said fluid regulating portion includes a slider and a fluid regulating aperture, said slider being configured to travel within said fluid regulating aperture.

13. The segment of claim 1, wherein a proximal end of said body has a shape different from a distal end of said body for mounting the segment in the fluid pump in a proper orientation.

14. The segment of claim 1, wherein said body includes a base, a membrane, a cover, an input port and an output port, said membrane being disposed between said cover and said base, said base and said membrane defining a fluid flow channel, and said input port and said output port being axially aligned.

15. The segment of claim 14, wherein the width of said membrane across said base and the depth of said fluid flow channel are selected to control the change in volume between said membrane and said base in the case where fluid pressure upstream of the segment should vary.

16. The segment of claim 1, further comprising a pressure sensing input channel disposed between said pumping portion and said pressure sensor interfacing portion, the length and width of said pressure sensing channel being selected to reduce transmission of fluid disturbances caused by the fluid pump acting on said pumping portion from reaching said pressure sensor interfacing portion.

17. The segment of claim 1, further comprising mounting flanges configured along a length of said body, said mounting flanges configured to be received by a clamping mechanism of the fluid pump for securing the segment in a predetermined position to the pump.

18. The segment of claim 1, wherein said body includes a first rigid fitting and a second rigid fitting, said input port associated with said first rigid fitting and said output port associated with said second rigid fitting.

19. A fluid conducting segment for infusing fluids to a patient and for use with a fluid pump that acts on the segment for controlled fluid flow to the patient, the segment comprising:
   a pumping portion;
   a fluid regulation;
   a pressure interfacing portion;
   a base having a first open end and a second open end, said first and second open ends each adapted to connect with conventional tubing, a groove extending along the length of said base between the open ends, and a fluid controlled region;
   a membrane having an upper surface and a lower surface, said upper and lower surfaces each having a central planar region, and a pressure vessel extending a predetermined distance from said upper surface;
   a cover having a pressure vessel aperture, a pumping aperture and a fluid regulation aperture;
   said membrane being disposed between said base and said cover;
   said base and said membrane defining a fluid flow channel placing said first open end in fluid communication with said second open end; and
   a sliding flow controller adapted to longitudinally travel along a portion of said base, said sliding flow controller engaging the membrane with the control region of the base to control the flow of fluid through the segment.

20. The segment of claim 19, wherein said membrane cooperates with said pumping aperture and said channel to define said pumping portion of the segment.

21. The segment of claim 19, wherein said membrane cooperates with said fluid regulation aperture, said fluid control region and said slider to define said fluid regulation portion of the segment.

22. The segment of claim 19, wherein said pressure vessel cooperates with said pressure vessel aperture and said channel to define said pressure sensor interfacing portion of the segment.

23. The segment of claim 19, said base further comprising click stops cooperating with said slider to indicate that said slider is in a flow stop position.

24. The segment of claim 19, wherein said base has an oval shape, a proximal end, a distal end, a mid-section, a bottom portion, a base sidewall projecting substantially perpendicularly from said bottom portion and around a perimeter of thereof, said bottom portion and said base sidewall defining a base interior, a flange formed substantially about said distal end and said mid-section and projecting substantially perpendicularly from a top of said base sidewall and away from said base interior, said flange adapted to limit longitudinal travel of said slider, a membrane recess formed in said base interior and adapted to receive associated structure of said membrane and a cover recess formed in said base interior and adapted to receive associated structure of said cover.

25. The segment of claim 24 wherein said flange has rectangular notches formed therein, said notches facilitating proper positioning of the segment into the pumping system.

26. The segment of claim 24 wherein said cover has an elongated oval shape, a top portion, a cover sidewall projecting substantially perpendicularly from said top portion and around a perimeter thereof, said top portion and said cover sidewall defining a cover interior, said cover sidewall adapted to mate with said cover recess, and a membrane cavity formed in said cover interior and adapted to receive associated structure of said membrane.

27. The segment of claim 26 wherein said membrane is made from a resilient elastomeric material and has an elongated oval shape, an upper sidewall projecting substantially perpendicular from said upper surface and around a perimeter thereof, said upper sidewall adapted to sealingly mate with said membrane cavity and a lower sidewall projecting substantially perpendicular from said lower surface and around a perimeter thereof, said lower sidewall adapted to sealingly mate with said membrane recess.

28. The segment of claim 27 wherein the seal of the membrane with the base and cover comprises a self-energizing seal.

29. The segment of claim 19, wherein said central planar region of said lower surface of said membrane overlays said groove and said fluid control region formed in said groove, and an underside of said vessel of said membrane overlays said groove.

30. The segment of claim 29, wherein said pumping aperture of said cover and said fluid regulation aperture of said cover are adapted to provide access to said central planar region of said upper surface of said membrane and said pressure vessel aperture is adapted to provide access to said pressure vessel.

31. The segment of claim 30 wherein said projection of said slider is adapted to travel within said fluid regulation aperture and adapted to engage said upper surface of said membrane.

32. The segment of claim 19 wherein a proximal end of the segment has a shape different from the distal end of the segment for mounting the segment in a pumping mechanism in a proper orientation.

33. The segment of claim 19 wherein the width of the membrane across the base and the depth of the channel are selected to control the change in volume between the membrane and base in the case where fluid pressure upstream of the segment should vary.

34. The segment of claim 19 further comprising a pressure sensing input channel disposed between the pumping section of the segment and the pressure sensing section of the segment, the length and width of the pressure sensing channel being selected to reduce the transmission of fluid disturbances caused by a pumping mechanism acting on the pumping section from reaching the pressure sensing section.

35. A fluid conducting segment for infusing fluids to a patient and for use with a flow control device that acts on the segment for controlled fluid flow to the patient, the segment comprising:
   a body having:
      a pumping portion;
      a fluid regulation portion;
      a pressure sensor interfacing portion;
      an input port;
      an output port; and
      a slider mounted to said body portion;
wherein said slider engages said fluid regulation portion for providing variable flow control.

36. The segment of claim 35, wherein said slider is configured to longitudinally travel along a portion of said body.

37. The segment of claim 36, wherein said slider can be configured in a flow position, a flow stop position and a plurality of positions therebetween each of which having a different flow associated therewith.

38. The segment of claim 36, said body further comprising click stops cooperating with said slider to indicate that said slider is in a flow stop position.

39. The segment of claim 36, wherein said slider includes a digit engaging device for manual control of the position of said slider.

40. The segment of claim 35, wherein said slider includes engaging means cooperating with the flow control device such that the flow control device automatically controls positioning of said slider.

41. The segment of claim 36, wherein said body includes a base, a membrane and a cover, said membrane being disposed between said base and said cover and said membrane and said base defining a fluid path.

42. The segment of claim 41, wherein said slider includes a projection, said projection operating to engage said membrane and to control the fluid path defined by said membrane and said base.

43. The segment of claim 42, wherein said projection comprises a ball.

44. The segment of claim 42, wherein said membrane includes a concavity for receiving said projection when said slider is placed in a full flow position.

45. The segment of claim 42, said base including a longitudinal groove, said slider projection operating to depress said membrane against said portion of said base including said groove.

46. The segment of claim 35, wherein said input and output ports are in axial alignment.

47. A fluid conducting segment for use with a fluid pump that acts as the segment for controlled fluid flow to a patient, the segment comprising:
   a rigid body portion having:
      a pumping portion;
      a fluid regulation portion;
      a pressure sensor interfacing portion;
      an input port; and
      an output port;
wherein said ports are in axial alignment.

48. The segment of claim 47, further comprising a slider that engages said fluid regulation portion to control flow through the segment.

49. The segment of claim 48, wherein said slider comprises a ball, said ball cooperating with said fluid regulation portion to control flow through the segment.

50. The segment of claim 48, wherein said slider is configured to longitudinally travel along a portion of said body.

51. The segment of claim 48, wherein said slider accomplishes variable flow control.

52. The segment of claim 48, wherein said slider is positionable in a flow position and in a flow stop position.

53. A fluid conducting segment for use with a fluid pump that acts as the segment for controlled fluid flow to a patient, the segment comprising:

a rigid body portion having:
    a pumping portion;
    a fluid regulation portion;
    a pressure sensor interfacing portion;
    an input port; and
    an output port;
  wherein said ports are located at opposing ends of said body.

54. The segment of claim 53, further comprising a slider that engages said fluid regulation portion to control flow through the segment.

55. The segment of claim 54, wherein said slider is positionable in flow position and in a flow stop position.

56. The segment of claim 55, wherein said slider accomplishes variable flow control.

57. The segment of claim 56, wherein said slider is configured to longitudinally travel along a portion of said body.

* * * * *